United States Patent
Astrid et al.

(10) Patent No.: US 10,407,650 B2
(45) Date of Patent: Sep. 10, 2019

(54) DETERGENT COMPOSITIONS COMPRISING A PROTEASE

(71) Applicant: Novozymes A/S, Bagsvaerd (DK)

(72) Inventors: Benie Astrid, Vaerloese (DK); Jeppe Wegener Tams, Gentofte (DK); Peter Rahbek Oestergaard, Virum (DK); Morten Gjermansen, Greve (DK); Martin Simon Borchert, Hilleroed (DK)

(73) Assignee: NOVOZYMES A/S, Bagsvaerd (DK)

( * ) Notice: Subject to any disclaimer, the term of this patent is extended or adjusted under 35 U.S.C. 154(b) by 239 days.

(21) Appl. No.: 14/391,572

(22) PCT Filed: May 1, 2013

(86) PCT No.: PCT/EP2013/059077
§ 371 (c)(1),
(2) Date: Oct. 9, 2014

(87) PCT Pub. No.: WO2013/164379
PCT Pub. Date: Nov. 7, 2013

(65) Prior Publication Data
US 2015/0104856 A1 Apr. 16, 2015

Related U.S. Application Data

(60) Provisional application No. 61/640,920, filed on May 1, 2012.

(30) Foreign Application Priority Data

May 1, 2012 (EP) .................................... 12166289

(51) Int. Cl.
*C12N 9/50* (2006.01)
*C12N 9/52* (2006.01)
*C11D 3/386* (2006.01)

(52) U.S. Cl.
CPC ...... *C11D 3/38618* (2013.01); *C11D 3/38609* (2013.01); *C12N 9/50* (2013.01); *C12N 9/52* (2013.01)

(58) Field of Classification Search
CPC .................................... C12N 9/50; C12N 9/52
See application file for complete search history.

(56) References Cited

U.S. PATENT DOCUMENTS

| | | | | |
|---|---|---|---|---|
| 2002/0142934 A1* | 10/2002 | Khan | ...................... | C11D 3/386 510/392 |
| 2004/0038845 A1* | 2/2004 | Pedersen | ................ | C11D 3/386 510/392 |
| 2007/0189919 A1* | 8/2007 | Prince | ............... | A61M 15/0085 422/28 |

FOREIGN PATENT DOCUMENTS

| | | |
|---|---|---|
| WO | 98/13459 A1 | 4/1998 |
| WO | 2004/033668 A2 | 4/2004 |
| WO | 2007/141736 A2 | 12/2007 |
| WO | 2009/118375 A2 | 10/2009 |

OTHER PUBLICATIONS

UniProt_201606 database Acc#E8WE14 from Lucas et al, 2011. Alignment with SEQ ID No. 2.*
UniParc, 2010 Acc#D1XSD4.*
Royal Society of Chemistry, Surfactants: the ubiquitous amphiphiles. Downloaded Mar. 13, 2014.*
Ecological Surfactants, Saponins. Downloaded Mar. 13, 2014.*
USPTO in house BLAST aligment of SEQ ID No. 2 with B. lentus subtilisin Acc#1ST3_A. Performed May 15, 2017.*
Dawn Ultra Concentrated Dishwashing Liquid, Ingredients. Down loaded Oct. 3, 2018.*
Donlon, 2007, Indu Enzy Stru Fun and App, pp. 197-206.
Lucas et al, 2012—Uniprot G2NG93.
Stoner et al. Enzyme and Microbial Technology 34 (2004) 114-125.
Lund et al. J Surfact Deterg (2012) 15:9-21.
Qin et al, 2011, GenBank No. EHM23718.

* cited by examiner

*Primary Examiner* — Sheridan Swope
(74) *Attorney, Agent, or Firm* — David Fazzolare

(57) ABSTRACT

A detergent composition comprising a polypeptide having protease activity is disclosed. The composition may be used in laundry or hard surface cleaning such as automated dish wash, and it has improved performance compared with a commercial protease.

16 Claims, 2 Drawing Sheets
Specification includes a Sequence Listing.

DETERGENT COMPOSITIONS COMPRISING A PROTEASE

CROSS-REFERENCE TO RELATED APPLICATIONS

This application is a 35 U.S.C. 371 national application of PCT/EP2013/059077 filed May 1, 2013, which claims priority or the benefit under 35 U.S.C. 119 of European application no. 12166289.4 filed May 1, 2012 and U.S. provisional application No. 61/640,920 filed May 1, 2012 the contents of which are fully incorporated herein by reference.

REFERENCE TO A SEQUENCE LISTING

This application contains a Sequence Listing in computer readable form, which is incorporated herein by reference.

BACKGROUND OF THE INVENTION

The detergent industry has for many years implemented different enzymes in detergent formulations, most commonly used enzymes includes proteases, amylases and lipases each adapted for removing various types of stains. In addition to the enzymes detergent compositions typically include a complex combination of ingredients. For example, most cleaning products include surfactant system, bleaching agents or builders. Despite the complexity of current detergents, there remains a need for developing new detergent compositions comprising new enzymes and/or enzyme blends.

Traditionally laundering has been done at elevated temperatures and pH and well known detergent enzymes have been selected to perform at higher temperatures and pH, typically in the range of 40° C.-60° C.

The increased focus on improving the washing processes in order to make them more environmental friendly has resulted in a global tendency to lowering wash time, pH, temperature and decreasing the amount of detergent components which may influence the environment negatively.

Thus, there is a desire also to launder at lower temperature, lower pH and/or lower amount of detergent components and therefore a need for detergent proteases which in addition to perform well under traditional conditions e.g. elevated temperature, pH and high amount of detergent components also have high performance e.g. at low temperatures and/or low pH. In addition, there is a need for enzymes performing in various detergents such as detergents with low amount of surfactant and builders.

The present invention is directed to these and other important ends.

FIELD OF THE INVENTION

The present invention relates to cleaning and/or detergent compositions comprising a polypeptides having protease activity. The invention further relates use of such polypeptides having protease activity in cleaning processes, such as dish wash and laundry. The invention also relates to a polynucleotide encoding the polypeptide, nucleic acid constructs, vectors, and host cells comprising the polynucleotides as well as methods of producing and using the polypeptides.

SUMMARY OF THE INVENTION

In one aspect, the invention relates to the use of a polypeptide having protease activity in a cleaning process, wherein the polypeptide having protease activity is selected among:

a) a polypeptide having at least 60% sequence identity, such as at least 70% identity, preferably at least 75% identity, preferably at least 80% identity, preferably at least 85% sequence identity, preferably at least 90% identity, preferably at least 95% identity, preferably at least 97% identity, preferably at least 98% identity and most preferred at least 99% identity to the mature polypeptide of SEQ ID NO: 2;

(b) a polypeptide encoded by a polynucleotide having at least 60% sequence identity such as at least 70% identity, preferably at least 75% identity, preferably at least 80% identity, preferably at least 85% sequence identity, preferably at least 90% identity, preferably at least 95% identity, preferably at least 97% identity, preferably at least 98% identity and most preferred at least 99% identity to the mature polypeptide coding sequence of SEQ ID NO: 1;

(c) a variant comprising a substitution, deletion, and/or insertion of one or more (several) amino acids of the mature polypeptide of SEQ ID NO: 2; and (d) a fragment of a polypeptide of (a), (b) or (c) that has protease activity.

In another aspect, the invention relates to a detergent composition comprising the polypeptide having protease activity in a cleaning process. The cleaning process may be laundering of fabrics or textiles or it may be dish was such as autiomated dish wash.

In further aspects, the invention relates to polynucleotides encoding the polypeptide having protease activity, nucleic acid constructs, such as expression constructs, comprising such a polynucleotide, host cells comprising such a construct and method for producing the polypeptide having protease activity by use of such a polynucleotide and/or nucleic acid construct.

Another aspect concerns a detergent composition comprising one or more detergent components and a polypeptide having protease activity wherein the polypeptide having protease activity is selected among:

a) a polypeptide having at least 70% sequence identity, such as at least 75% sequence identity, at least 80% sequence identity, at least 85% sequence identity, at least 90% sequence identity, at least 95% sequence identity, at least 97% sequence identity, at least 98% sequence identity, at least 99% sequence identity or 100% sequence identity to the mature polypeptide of SEQ ID NO: 2;

(b) a polypeptide encoded by a polynucleotide having at least 70% sequence identity, such as at least 75% sequence identity, at least 80% sequence identity, at least 85% sequence identity, at least 90% sequence identity, at least 95% sequence identity, at least 97% sequence identity, at least 98% sequence identity, at least 99% sequence identity or 100% sequence identity to the mature polypeptide coding sequence of SEQ ID NO: 1;

(c) a variant comprising a substitution, deletion, and/or insertion of one or more (several) amino acids of the mature polypeptide of SEQ ID NO: 2, wherein said variant having at least 70% sequence identity, such as at least 75% sequence identity, at least 80% sequence identity, at least 85% sequence identity, at least 90% sequence identity, at least 95% sequence identity, at least 97% sequence identity, at least 98% sequence identity, at least 99% sequence identity, but having less than 100% sequence identity to the mature polypeptide of SEQ ID NO 2; and
  (d) a fragment of a polypeptide of (a), (b) or (c) that has protease activity.

Another aspect relates to a method for degrading or removing proteinaceous materials from a textile or a hard surface comprising treating the textile or the hard surface with a composition according to the invention.

Yet another aspect of the invention relates to the use in a detergent composition of a polypeptide having protease activity, selected from the group consisting of:
  a) a polypeptide having at least 70% sequence identity, such as at least 75% sequence identity, at least 80% sequence identity, at least 85% sequence identity, at least 90% sequence identity, at least 95% sequence identity, at least 97% sequence identity, at least 98% sequence identity, at least 99% sequence identity or 100% sequence identity to the mature polypeptide of SEQ ID NO: 2;
  (b) a polypeptide encoded by a polynucleotide that hybridizes under high stringency conditions, or very high stringency conditions with
    (i) the mature polypeptide coding sequence of SEQ ID NO: 1;
    (ii) the full-length complementary strand of (i);
  (c) a polypeptide encoded by a polynucleotide having at least 70% sequence identity, such as at least 75% sequence identity, at least 80% sequence identity, at least 85% sequence identity, at least 90% sequence identity, at least 95% sequence identity, at least 97% sequence identity, at least 98% sequence identity, at least 99% sequence identity or 100% sequence identity to the mature polypeptide coding sequence of SEQ ID NO: 1;
  (d) a variant comprising a substitution, deletion, and/or insertion of one or more (several) amino acids of the mature polypeptide of SEQ ID NO: 2, wherein said variant having at least 70% sequence identity, such as at least 75% sequence identity, at least 80% sequence identity, at least 85% sequence identity, at least 90% sequence identity, at least 95% sequence identity, at least 97% sequence identity, at least 98% sequence identity, at least 99% sequence identity, but having less than 100% sequence identity to the mature polypeptide of SEQ ID NO 2; and
  (e) a fragment of a polypeptide of (a), (b), (c) or (d), that has protease activity.

A third aspect of the invention relates to the use in a cleaning process such as laundry or dishwash of an isolated polypeptide having protease activity selected among:
  a) a polypeptide having at least 70% sequence identity, such as at least 75% sequence identity, at least 80% sequence identity, at least 85% sequence identity, at least 90% sequence identity, at least 95% sequence identity, at least 97% sequence identity, at least 98% sequence identity, at least 99% sequence identity or 100% sequence identity to the mature polypeptide of SEQ ID NO: 2;
  (b) a polypeptide encoded by a polynucleotide that hybridizes under high stringency conditions, or very high stringency conditions with
    (i) the mature polypeptide coding sequence of SEQ ID NO: 1;
    (ii) the full-length complementary strand of (i);
  (c) a polypeptide encoded by a polynucleotide having at least 70% sequence identity, such as at least 75% sequence identity, at least 80% sequence identity, at least 85% sequence identity, at least 90% sequence identity, at least 95% sequence identity, at least 97% sequence identity, at least 98% sequence identity, at least 99% sequence identity or 100% sequence identity to the mature polypeptide coding sequence of SEQ ID NO: 1;
  (d) a variant comprising a substitution, deletion, and/or insertion of one or more (several) amino acids of the mature polypeptide of SEQ ID NO: 2, wherein said variant having 70% sequence identity, such as at least 75% sequence identity, at least 80% sequence identity, at least 85% sequence identity, at least 90% sequence identity, at least 95% sequence identity, at least 97% sequence identity, at least 98% sequence identity, at least 99% sequence identity, but having less than 100% sequence identity to the mature polypeptide of SEQ ID NO 2; and
  (e) a fragment of a polypeptide of (a), (b), (c) or (d), that has protease activity.

In further aspects, the invention relates to polynucleotides encoding the polypeptide having protease activity, nucleic acid constructs, such as expression constructs, comprising such a polynucleotide, host cells comprising such a construct and method for producing the polypeptide having protease activity by use of such a polynucleotide and/or nucleic acid construct.

BRIEF DESCRIPTION OF THE FIGURES

The FIGS. 1-4 show results of the characterization of the S8 protease derived from *Streptomyces* sp. ACTE (the mature polypeptide of SEQ ID NO: 2) for experimental details see example 4.

OVERVIEW OF SEQUENCE LISTING

Figure 1:
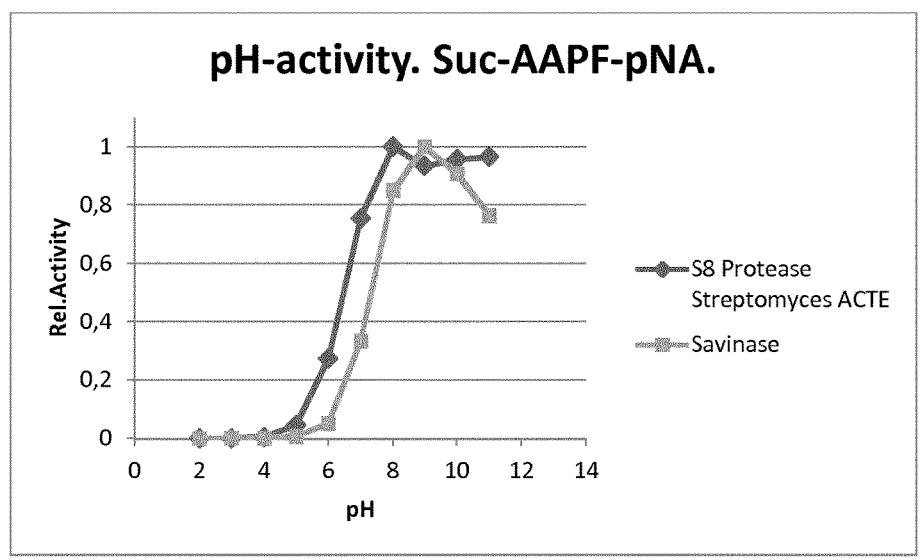
FIG. 1 shows the pH-activity on Suc-AAPF-pNA substrate.

SEQ ID NO: 1 is the DNA sequence of the *Bacillus* codon usage optimized fusion gene of the coding polynucleotides of the *Streptomyces* sp. ACTE protease with the natural signal peptide replaced with that of the *Bacillus lentus* Savinase protease.
SEQ ID NO: 2 is the amino acid sequence as deduced from SEQ ID NO: 1.
SEQ ID NO: 3 is the amino acid sequence of Savinase (protease from *Bacillus lentus*, Available from Novozymes A/S, Denmark)

Definitions

Polypeptides Having Protease Activity:
Polypeptides having protease activity, or proteases, are sometimes also designated peptidases, proteinases, peptide hydrolases, or proteolytic enzymes. Proteases may be of the exo-type that hydrolyses peptides starting at either end thereof or of the endo-type that act internally in polypeptide chains (endopeptidases). Endopeptidases show activity on N- and C-terminally blocked peptide substrates that are relevant for the specificity of the protease in question.

The term "protease" is defined herein as an enzyme that hydrolyses peptide bonds. This definition of protease also applies to the protease-part of the terms "parent protease" and "protease variant," as used herein. The term "protease" includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1-5 published in Eur. J. Bio-chem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The nomenclature is regularly supplemented and updated; see e.g. the World Wide Web (WWW) at http://www.chem.qmw.ac.uk/iubmb/enzyme/index.html.

The present invention provides for the use of polypeptides having protease activity in detergent compositions. It also provides polypeptides having protease activity and polynucleotides encoding the polypeptides. The proteases of the invention are serine proteases of the peptidase family S8. The proteases of the invention are active on Suc-Ala-Ala-Pro-Phe-pNA within a broad range from pH 4-11 and exhibit especially high activity in the range pH 6-11.

The proteases of the invention and for use according to the invention are selected from the group consisting of:
(a) proteases belonging to the EC 3.4.21 enzyme group; and/or
(b) Serine proteases of the peptidase family S8;
as described in Biochem. J. 290:205-218 (1993) and in MEROPS protease database, release, 9.4 (31 Jan. 2011) (www.merops.ac.uk). The database is described in Rawlings, N. D., Barrett, A. J. & Bateman, A. (2010) 'MEROPS: the peptidase database', *Nucleic Acids Res* 38, D227-D233.

Proteases of the invention are endopeptidases (EC 3.4.21). There are several protease activity types: The three main activity types are: trypsin-like where there is cleavage of amide substrates following Arg or Lys at P1, chymotrypsin-like where cleavage occurs following one of the hydrophobic amino acids at P1, and elastase-like with cleavage following an Ala at P1.

For determining whether a given protease is a serine protease, and a family S8 protease, reference is made to the above Handbook and the principles indicated therein. Such determination can be carried out for all types of proteases, be it naturally occurring or wild-type proteases; or genetically engineered or synthetic proteases.

The peptidases of family S8 contain the catalytic triad Asp, His and Ser in that order. Mutation of any of the amino acids of the catalytic triad will result in change or loss of enzyme activity. The amino acids of the catalytic triad of the S8 protease as isolated from *Streptomyces* sp. ACTE (SEQ ID NO: 2) are probably positions Asp 40, His 73 and Ser 225.

Protease activity can be measured using any assay, in which a substrate is employed, that includes peptide bonds relevant for the specificity of the protease in question. Examples of general protease substrates are casein, bovine serum albumin and haemoglobin. In the classical Anson and Mirsky method, denatured haemoglobin is used as substrate and after the assay incubation with the protease in question, the amount of trichloroacetic acid soluble haemoglobin is determined as a measurement of protease activity (Anson, M. L. and Mirsky, A. E., 1932, *J. Gen. Physiol.* 16: 59 and Anson, M. L., 1938, *J. Gen. Physiol.* 22: 79).

For the purpose of the present invention, protease activity was determined using assays which are described in "Materials and Methods", such as the Kinetic Suc-AAPF-pNA assay, Protazyme AK assay and Kinetic Suc-AAPX-pNA assay. For the Protazyme AK assay, insoluble Protazyme AK (Azurine-Crosslinked Casein) substrate liberates a blue colour when incubated with the protease and the colour is determined as a measurement of protease activity. For the Suc-AAPF-pNA assay, the colourless Suc-AAPF-pNA substrate liberates yellow paranitroaniline when incubated with the protease and the yellow colour is determined as a measurement of protease activity. The polypeptides of the present invention have at least 20%, e.g., at least 40%, at least 50%, at least 60%, at least 70%, at least 80%, at least 90%, at least 95%, and at least 100% of the protease activity of the mature polypeptide of SEQ ID NO: 2.

Isolated polypeptide: The term "isolated polypeptide" means a polypeptide that is modified by the hand of man relative to that polypeptide as found in nature, whereby it has been completely or partially separated from at least one other compound with which the polypeptide is found in nature. In one aspect, the polypeptide is at least 1% pure, e.g., at least 5% pure, at least 10% pure, at least 20% pure, at least 40% pure, at least 60% pure, at least 80% pure, and at least 90% pure, as determined by SDS-PAGE.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99% pure, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 279 of SEQ ID NO: 2 based on sequencing using Edman degradation and intact molecular weight analysis. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Propeptide: The term "propeptide" means a polypeptide that is translated together with the mature polypeptide and are cleaved of before the mature polypeptide is released and obtain protease activity. In one aspect the propeptide is amino acids −89 to −1 of SEQ ID NO: 2.

Signal peptide: The term "Signal peptide" means a short polypeptide that is translated together with the mature polypeptide and the propeptide if present. The signal peptide is located in the N-terminus of the translated polypeptide and is responsible for the secretion of the polypeptide. Usually the signal peptide is removed during translocation of the polypeptide across a membrane, such as a plasma membrane or the membrane of the endoplasmatic reticulum.

Signal peptides are well known in the art and several methods for predicting signal peptides have been developed e.g., SignalP (Nielsen et al., 1997, *Protein Engineering* 10: 1-6)]. In one aspect the signal sequence is amino acids −116 to −90 of SEQ ID NO:2.

Mature polypeptide coding sequence: The term "mature polypeptide coding sequence" means a polynucleotide that encodes a mature polypeptide having protease activity. In one aspect, the mature polypeptide coding sequence is nucleotides 349 to 1085 of SEQ ID NO: 1 based on the SignalP (Nielsen et al., 1997, *Protein Engineering* 10: 1-6) prediction program that also predicts nucleotides 1 to 81 of SEQ ID NO: 1 encode a signal peptide. In another aspect, the mature polypeptide coding sequence is nucleotides 349 to 1185 of SEQ ID NO: 1 based on sequencing using Edman degradation and intact molecular weight analysis of the mature polypeptide.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, Trends Genet. 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the −nobrief option) is used as the percent identity and is calculated as follows:

(Identical Residues−100)/(Length of Alignment−
Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the −nobrief option) is used as the percent identity and is calculated as follows:

(Identical Deoxyribonucleotides=100)/(Length of
Alignment−Total Number of Gaps in Alignment)

Fragment: The term "fragment" means a polypeptide having one or more (several) amino acids deleted from the amino and/or carboxyl terminus of a mature polypeptide; wherein the fragment has protease activity. In one aspect, a fragment contains at least 200 amino acid residues (e.g., amino acids 50 to 250 of SEQ ID NO: 2), at least 230 amino acid residues (e.g., amino acids 20 to 250 of SEQ ID NO: 2), at least 260 amino acid residues (e.g., amino acids 15 to 275 of SEQ ID NO: 2) and at least 275 amino residues (e.g. amino acids 1 to 275 of SEQ ID NO: 2).

Subsequence: The term "subsequence" means a polynucleotide having one or more (several) nucleotides deleted from the 5' and/or 3' end of a mature polypeptide coding sequence; wherein the subsequence encodes a fragment having protease activity. In one aspect, a subsequence contains at least 600 nucleotides (e.g., nucleotides 496 to 1098 of SEQ ID NO: 1), e.g., at least 690 nucleotides (e.g., nucleotides 406 to 1098 of SEQ ID NO: 1), at least 780 nucleotides (e.g., nucleotides 391 to 1173 of SEQ ID NO: 1), and at least 825 nucleotides (e.g., nucleotides 391 to 1173 of SEQ ID NO: 1).

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" means a polynucleotide that is modified by the hand of man relative to that polynucleotide as found in nature whereby it has been completely or partially separated from at least one other compound with which the polypeptide is found in nature. In one aspect, the isolated polynucleotide is at least 1% pure, e.g., at least 5% pure, more at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

Substantially pure polynucleotide: The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5' and 3' untranslated regions, such as promoters and terminators. Preferably, the polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

Coding sequence: The term "coding sequence" means a polynucleotide, which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" means all components necessary for the expression of a polynucleotide encoding a polypeptide of the present invention. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of the polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to additional nucleotides that provide for its expression.

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Variant: The term "variant" means a polypeptide having protease activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding e.g. 1-3 amino acids adjacent to an amino acid occupying a position.

Cleaning composition: The terms "cleaning compositions" and "cleaning formulations," refer to compositions that find use in the removal of undesired compounds from items to be cleaned, such as fabric, carpets, dishware including glassware, contact lenses, hard surfaces such as tiles, zincs, floors, and table surfaces, hair (shampoos), skin (soaps and creams), teeth (mouthwashes, toothpastes), etc. The terms encompasses any materials/compounds selected for the particular type of cleaning composition desired and the form of the product (e.g., liquid, gel, granule, or spray compositions), as long as the composition is compatible with the protease and other enzyme(s) used in the composition. The specific selection of cleaning composition materials is readily made by considering the surface, item or fabric to be cleaned, and the desired form of the composition for the cleaning conditions during use. These terms further refer to any composition that is suited for cleaning, bleaching, disinfecting, and/or sterilizing any object and/or surface. It is intended that the terms include, but are not limited to detergent composition (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish detergents).

Detergent composition: The term "detergent composition", includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, car or carpet shampoos, bathroom cleaners; hair shampoos and hair-rinses; shower gels, foam baths; metal cleaners; as well as cleaning auxiliaries such as bleach additives and "stain-stick" or pre-treat types.

The terms "detergent composition" and "detergent formulation" are used in reference to mixtures which are intended for use in a wash medium for the cleaning of soiled objects. In some embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the present invention be limited to any particular detergent formulation or composition. It is intended that in addition to the protease according to the invention, the term encompasses detergents that contains, e.g., surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, anti-oxidants, and solubilizers.

Enzyme Detergency benefit: The term "enzyme detergency benefit" is defined herein as the advantageous effect an enzyme may add to a detergent compared to the same detergent without the enzyme. Important detergency benefits which can be provided by enzymes are stain removal with no or very little visible soils after washing and or cleaning, prevention or reduction of redeposition of soils released in the washing process an effect that also is termed anti-redeposition, restoring fully or partly the whiteness of textiles, which originally were white but after repeated use and wash have obtained a greyish or yellowish appearance an effect that also is termed whitening. Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric an effect that is also termed dye transfer inhibition or anti-backstaining, removal of protruding or broken fibers from a fabric surface to decrease pilling tendencies or remove already existing pills or fuzz an effect that also is termed anti-pilling, improvement of the fabric-softness, colour clarification of the fabric and removal of particulate soils which are trapped in the fibers of the fabric or garment. Enzymatic bleaching is a further enzyme detergency benefit where the catalytic activity generally is used to catalyse the formation of bleaching component such as hydrogen peroxide or other peroxides.

Textile care benefit: Textile care benefits, which are not directly related to catalytic stain removal or prevention of redeposition of soils, are also important for enzyme detergency benefits. Examples of such textile care benefits are prevention or reduction of dye transfer from one textile to another textile or another part of the same textile an effect that is also termed dye transfer inhibition or anti-backstaining, removal of protruding or broken fibers from a textile surface to decrease pilling tendencies or remove already existing pills or fuzz an effect that also is termed anti-pilling, improvement of the textile-softness, colour clarification of the textile and removal of particulate soils which are trapped in the fibers of the textile. Enzymatic bleaching is a further enzyme detergency benefit where the catalytic activity generally is used to catalyze the formation of bleaching component such as hydrogen peroxide or other peroxides or other bleaching species.

Delta remission value (ΔRem): The terms "Delta remission" or "Delta remission value" are defined herein as the result of a reflectance or remission measurement at 460 nm. The swatch is measured with one swatch of similar color as background, preferably a swatch from a repetition wash. A swatch representing each swatch type is measured before wash. The Delta remission is the remission value of the washed swatch minus the remission value of the unwashed swatch.

Delta enzyme performance value (ΔRem enzyme value): The term "Delta enzyme remission value" is defined herein as the result of a reflectance or remission measurement at 460 nm. The swatch is measured with one swatch of similar color as background, preferably a swatch from a repetition wash. A swatch representing each swatch type is measured before wash. The Delta remission is the remission value of the swatch washed in detergent with an enzyme present minus the remission value of a similar swatch washed in a detergent without enzyme present.

Detergent component: the term "detergent component" is defined herein to mean the types of chemicals which can be used in detergent compositions. Examples of detergent components are surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers. The detergent composition may comprise of one or more of any type of detergent component.

Dish wash: The term "dish wash" refers to all forms of washing dishes, e.g. by hand or automatic dish wash. Washing dishes includes, but is not limited to, the cleaning of all forms of crockery such as plates, cups, glasses, bowls, all forms of cutlery such as spoons, knives, forks and serving utensils as well as ceramics, plastics, metals, china, glass and acrylics.

Dish washing composition: The term "dish washing composition" refers to all forms of compositions for cleaning hard surfaces. The present invention is not restricted to any particular type of dish wash composition or any particular detergent.

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and toweling. The textile may be cellulose based such as natural cellulosics, including cotton, flax/linen, jute, ramie, sisal or coir or manmade cellulosics (e.g. originating from wood pulp) including viscose/rayon, ramie, cellulose acetate fibers (tricell), lyocell or blends thereof. The textile or fabric may also be non-cellulose based such as natural polyamides including wool, camel, cashmere, mohair, rabit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g. polyamide fibers, acrylic fibers, polyester fibers, polyvinyl alcohol fibers, polyvinyl chloride fibers, polyurethane fibers, polyurea fibers, aramid fibers), and cellulose-containing fibers (e.g. rayon/viscose, ramie, flax/linen, jute, cellulose acetate fibers, lyocell). Fabric may be conventional washable laundry, for example stained household laundry. When the term fabric or garment is used it is intended to include the broader term textiles as well.

Hard surface cleaning: The term "Hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but is not limited to cleaning of plates, cups, glasses, bowls, and cutlery such as spoons, knives, and forks, serving utensils, ceramics, plastics, metals, china, glass and acrylics.

Improved wash performance: The term "improved wash performance" is defined herein as alteration of the wash performance of a protease relative to the wash performance of a reference protease e.g. by increased stain removal. The term "wash performance" includes wash performance in laundry but also e.g. in dish wash.

Wash performance: The term "wash performance" is used as an enzyme's ability to remove stains present on the object to be cleaned during e.g. wash or hard surface cleaning.

DETAILED DESCRIPTION OF THE INVENTION

The invention relates to a polypeptide having protease activity selected among:

a) a polypeptide having at least 60% sequence identity, such as at least 70% identity, preferably at least 75% identity, preferably at least 80% identity, preferably at least 85% sequence identity, preferably at least 90% identity, preferably at least 95% identity, preferably at least 97% identity, preferably at least 98% identity and most preferred at least 99% identity to the mature polypeptide of SEQ ID NO: 2;

b) a polypeptide encoded by a polynucleotide having at least 60% sequence identity such as at least 70% identity, preferably at least 75% identity, preferably at least 80% identity, preferably at least 85% sequence identity, preferably at least 90% identity, preferably at least 95% identity, preferably at least 97% identity, preferably at least 98% identity and most preferred at least 99% identity to the mature polypeptide coding sequence of SEQ ID NO: 1;

c) a variant comprising a substitution, deletion, and/or insertion of one or more (several) amino acids of the mature polypeptide of SEQ ID NO: 2; and d) a fragment of a polypeptide of (a), (b) or (c) that has protease activity.

Such a polypeptide preferably comprises or consists of the amino acid sequence of SEQ ID NO: 2 or an allelic variant thereof; or is a fragment thereof having protease activity. In another aspect, the polypeptide comprises or consists of the mature polypeptide of SEQ ID NO: 2. In another preferred aspect, the polypeptide comprises or consists of amino acids 1 to 279 of SEQ ID NO: 2.

The invention relates to a cleaning composition, such as a detergent composition comprising one or more cleaning or detergent components and a polypeptide having protease activity wherein the polypeptide having protease activity is selected among:
  a) a polypeptide having at least 70% sequence identity, such as at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2;
  b) a polypeptide encoded by a polynucleotide that hybridizes under high stringency conditions, or very high stringency conditions with
    (i) the mature polypeptide coding sequence of SEQ ID NO: 1;
    (ii) the full-length complementary strand of (i);
  c) a polypeptide encoded by a polynucleotide having at least 70% sequence identity, such as at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1; and/or
  d) a variant comprising a substitution, deletion, and/or insertion of one or more (several) amino acids of the mature polypeptide of SEQ ID NO: 2, wherein said variant having at least at least 70% sequence identity, such as at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but having less than 100% sequence identity to the mature polypeptide of SEQ ID NO 2; and
  e) a fragment of a polypeptide of (a), (b), (c) or (d), which has protease activity.

The present invention relates to detergents compositions comprising one or more detergent components and comprising isolated polypeptides having a sequence identity to the mature polypeptide of SEQ ID NO: 2 of at least 70% sequence identity, such as at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity, which have protease activity. In one aspect, the polypeptides differ by no more than thirty-six amino acids, e.g., by thirty amino acids, by twenty-five amino acids, by twenty amino acids, by fifteen amino acids, by ten amino acids, by nine amino acids, by eight amino acids, by seven amino acids, by six amino acids, by five amino acids, by four amino acids, by three amino acids, by two amino acids, and by one amino acid from the mature polypeptide of SEQ ID NO: 2.

The present invention further relates to the use in detergent compositions of polypeptides having protease activity selected from the group consisting of:
  a) a polypeptide having at least 70% sequence identity, such as at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2;
  (b) a polypeptide encoded by a polynucleotide that hybridizes under high stringency conditions, or very high stringency conditions with
    (i) the mature polypeptide coding sequence of SEQ ID NO: 1;
    (ii) the full-length complementary strand of (i);
  (c) a polypeptide encoded by a polynucleotide having at least 70% sequence identity, such as at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1; and/or
  (d) a variant comprising a substitution, deletion, and/or insertion of one or more (several) amino acids of the mature polypeptide of SEQ ID NO: 2, wherein said variant having at least 70% sequence identity, such as at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but having less than 100% sequence identity to the mature polypeptide of SEQ ID NO 2; and
  (e) a fragment of a polypeptide of (a), (b), (c) or (d), which has protease activity The present invention relates to the use in detergents of isolated polypeptides having a sequence identity to the mature polypeptide of SEQ ID NO: 2 of at least 60% sequence identity, such as at least at least 70% sequence identity, such as at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity, which have protease activity. In one aspect, the polypeptides differ by no more than thirty-six amino acids, e.g., by thirty amino acids, by twenty-five amino acids, by twenty amino acids, by fifteen amino acids, by ten amino acids, by nine amino acids, by eight amino acids, by seven amino acids, by six amino acids, by five amino acids, by four amino acids, by three amino acids, by two amino acids, and by one amino acid from the mature polypeptide of SEQ ID NO: 2.

The present invention also relates to variants comprising a substitution, deletion, and/or insertion of one or more (or several) amino acids of the mature polypeptide of SEQ ID NO: 2, or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain. Preferably the variant has at least 60% sequence identity to the mature polypeptide of SEQ ID NO: 2; e.g., at least 65%, at least 70%, at least 75%, at least 80%, at least 85%, at least 90%, at least 95%, at least 96%, at least 97%, at least 98% at least 99% but less than 100% identity to the mature polypeptide of SEQ ID NO: 2.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to the parent polypeptide.

The amino acids Asp 40, His 73 and Ser 225 form the catalytic triade of the protease having SEQ ID NO: 2 and are therefore critical for the molecule and should not be modified. Thus, amino acid residues corresponding to Asp 40, His 73 and Ser 225 in SEQ ID NO: 2 should preferably not be modified. The catalytic residues have been determined by alignment with known S8 serine protease where it has been found that the catalytic residues are conserved in all such proteases.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, Gene 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The total number of amino acid substitutions, deletions and/or insertions of the mature polypeptide of SEQ ID NO: 2 are in one embodiment not more than 10, e.g., 1, 2, 3, 4, 5, 6, 7, 8 or 9.

The polypeptide may be hybrid polypeptide in which a portion of one polypeptide is fused at the N-terminus or the C-terminus of a portion of another polypeptide.

The polypeptide may be a fused polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The present invention also relates to isolated polypeptides having protease activity that are encoded by polynucleotides that hybridize under very low stringency conditions, low stringency conditions, medium stringency conditions, medium-high stringency conditions, high stringency conditions, or very high stringency conditions with the mature polypeptide coding sequence of SEQ ID NO: 1, or the full-length complementary strand thereof (J. Sambrook, E. F. Fritsch, and T. Maniatis, 1989, *Molecular Cloning, A Laboratory Manual*, 2d edition, Cold Spring Harbor, N.Y.).
Sources of Polypeptides Having Protease Activity A polypeptide having protease activity may be obtained from microorganisms of any genus, from plants, virus, or from an animal of any species. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. For example, the polypeptide may be a gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* polypeptide having protease activity, or a gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasma* polypeptide.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide.

In another aspect, the polypeptide is a *Streptococcus equisimilis, Streptococcus pyogenes, Streptococcus uberis*, or *Streptococcus equi* subsp. *Zooepidemicus* polypeptide.

In another aspect, the polypeptide is a *Streptomyces achromogenes, Streptomyces avermitilis, Streptomyces coelicolor, Streptomyces griseus*, or *Streptomyces lividans* polypeptide.

The polypeptide may also be a fungal polypeptide. For example, the polypeptide may be a yeast polypeptide such as a *Candida, Kluyveromyces, Pichia, Saccharomyces, Schizosaccharomyces*, or *Yarrowia* polypeptide; or a filamentous fungal polypeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula,* Leptospaeria, *Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide.

In another aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide.

In another aspect, the polypeptide is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei*, or *Trichoderma viride* polypeptide.

In another aspect, the polypeptide is a *Streptomyces* sp. polypeptide.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) using the above-mentioned probes. Techniques for isolating microorganisms from natural habitats are well known in the art.

The polynucleotide encoding the polypeptide may then be obtained by similarly screening a genomic or cDNA library of another microorganism or mixed DNA sample. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Polynucleotides

The present invention also relates to isolated polynucleotides encoding a polypeptide of the present invention.

The techniques used to isolate or clone a polynucleotide encoding a polypeptide are known in the art and include isolation from genomic DNA, preparation from cDNA, or a combination thereof. The cloning of the polynucleotides from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Bacillus*, or another or related organism and thus, for example, may be an allelic or species variant of the polypeptide encoding region of the polynucleotide.

The present invention also relates to isolated polynucleotides comprising or consisting of polynucleotides having a degree of sequence identity to the mature polypeptide coding sequence of SEQ ID NO: 1 of at least 60%, e.g., at least 65%, at least 70%, at least 75%, at least 80%, at least 85%, at least 90%, at least 95%, at least 96%, at least 97%, at least 98%, at least 99%, or 100%, which encode a polypeptide having protease activity.

Modification of a polynucleotide encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant may be constructed on the basis of the polynucleotide presented as the mature polypeptide coding sequence of SEQ ID NO: 1, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution see, e.g., Ford et al., 1991, *Protein Expression and Purification* 2: 95-107.

The present invention also relates to isolated polynucleotides encoding polypeptides of the present invention, which hybridize under very low stringency conditions, low stringency conditions, medium stringency conditions, medium-high stringency conditions, high stringency conditions, or very high stringency conditions with the mature polypeptide coding sequence of SEQ ID NO: 1, or the full-length complementary strand thereof; or allelic variants and subsequences thereof (Sambrook et al., 1989, supra), as defined herein.

Polynucleotides encoding polypeptides of the invention may also be designed based on knowledge to the genetic code and synthesized artificially using methods known in the art. In particular it is possible to design a polynucleotide encoding the polypeptide of the invention, where the codon usage of the polynucleotide is particular suited for a selected host organism. As an example of such a polynucleotide can be mentioned the polynucleotide having SEQ ID NO: 1, which is codon optimized for expression in *Bacillus* sp.

In one aspect, the polynucleotide comprises or consists of SEQ ID NO: 1, the mature polypeptide coding sequence of SEQ ID NO: 1 or a subsequence of SEQ ID NO: 1 that encodes a fragment of SEQ ID NO: 2 having protease activity, such as the polynucleotide of nucleotides 349 to 1185 of SEQ ID NO: 1.

Nucleic Acid Constructs

The present invention also relates to nucleic acid constructs comprising a polynucleotide of the present invention operably linked to one or more (several) control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, a polynucleotide that is recognized by a host cell for expression of a polynucleotide encoding a polypeptide of the present invention. The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American*, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter including a gene encoding a neutral alpha-amylase in Aspergilli in which the untranslated leader has been replaced by an untranslated leader from a gene encoding triose phosphate isomerase in Aspergilli; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and

*Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the host cell of choice may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (several) convenient restriction sites to allow for insertion or substitution of the polynucleotide encoding the polypeptide at such sites. Alternatively, the polynucleotide may be expressed by inserting the polynucleotide or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMRI permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more (several) control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any gram-positive or gram-negative bacterium. Gram-positive bacteria include, but not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but not limited to, *Campylobacter,*

*E. coli, Flavobacterium, Fusobacterium, Helicobacter, Ilyobacter, Neisseria, Pseudomonas, Salmonella,* and *Ureaplasma.*

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus,* and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol. (Praha)* 49: 399-405), by conjugation (see, e.g., Mazodier et al., 1989, *J. Bacteriol.* 171: 3583-3585) or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-207), by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium* Series No. 9, 1980).

The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete,* Phlebia, *Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023 and Yelton et al., 1984, *Proc. Natl. Acad. Sci. USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Bacillus*.

The present invention also relates to methods of producing a polypeptide of the present invention, comprising: (a) cultivating a recombinant host cell of the present invention under conditions conducive for production of the polypeptide; and (b) recovering the polypeptide.

The host cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

In an alternative aspect, the polypeptide is not recovered, but rather a host cell of the present invention expressing a polypeptide is used as a source of the polypeptide.

The present invention also relates to compositions comprising a polypeptide of the present invention. Preferably, the compositions are enriched in such a polypeptide. The term "enriched" indicates that the protease activity of the composition has been increased, e.g., with an enrichment factor of at least 1.1.

Detergent Compositions

In one embodiment, the invention is directed to detergent compositions comprising a polypeptide of the present invention in combination with one or more additional cleaning and/or detergent composition components. The choice of additional components is within the skill of the artisan and includes conventional ingredients, including the exemplary non-limiting components set forth below.

The choice of components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation since the component may have one or more additional functionalities which the skilled artisan will appreciate. The detergent composition may be suitable for the laundering of textiles such as e.g. fabrics, cloths or linen, or for cleaning hard surfaces such as e.g. floors, tables, or dish wash.

Enzyme Amounts in Detergent Compositions

In one embodiment of the present invention, the a polypeptide of the present invention may be added to a detergent composition in an amount corresponding to 0.0001-200 mg of enzyme protein, such as 0.0005-100 mg of enzyme protein, preferably 0.001-30 mg of enzyme protein, more preferably 0.005-8 mg of enzyme protein, even more preferably 0.01-2 mg of enzyme protein per liter of wash liquor.

A composition for use in automatic dishwash (ADW), for example, may include 0.0001%-50%, such as 0.001%-20%, such as 0.01%-10%, such as 0.05-5% of enzyme protein by weight of the composition.

A composition for use in laundry granulation, for example, may include 0.0001%-50%, such as 0.001%-20%, such as 0.01%-10%, such as 0.05%-5% of enzyme protein by weight of the composition.

A composition for use in laundry liquid, for example, may include 0.0001%-10%, such as 0.001-7%, such as 0.1%-5% of enzyme protein by weight of the composition.

The proteases of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid (4-FPBA), and the composition may be formulated as described in, for example, WO92/19709 and WO92/19708.

Other suitable stabilizing agents are peptide aldehyde protease inhibitor such as peptide aldehydes disclosed in WO2009/118375 or WO 2010/055052.

A polypeptide of the present invention may also be incorporated in the detergent formulations disclosed in WO97/07202, which is hereby incorporated by reference.

The composition may comprise a polypeptide of the present invention as the major enzymatic component, e.g., a mono-component composition. Alternatively, the composition may comprise multiple enzymatic activities, such as an amino peptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, e.g., *Aspergillus aculeatus, Aspergillus awamori, Aspergillus foetidus, Aspergillus fumigatus, Aspergillus japonicus, Aspergillus nidulans, Aspergillus niger*, or *Aspergillus oryzae; Fusarium*, e.g., *Fusarium bactridioides, Fusarium cerealis, Fusarium crookwellense, Fusarium culmorum, Fusarium graminearum, Fusarium graminum, Fusarium heterospo-*

*rum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides,* or *Fusarium venenatum; Humicola*, e.g., *Humicola insolens* or *Humicola lanuginosa*; or *Trichoderma*, e.g., *Trichoderma harzianum, Trichoderma koningii, Trichoderma longibrachiatum, Trichoderma reesei,* or *Trichoderma viride.*

The compositions may be prepared in accordance with methods known in the art and may be in the form of a liquid or a dry composition. For instance, the composition may be in the form of a granulate or a microgranulate. The polypeptide may be stabilized in accordance with methods known in the art.

Thus one aspect of the invention realtes to a detergent composition comprising one or more detergent components and a polypeptide having protease activity wherein the polypeptide having protease activity is selected among:

a) a polypeptide having at least 70% sequence identity, such as at least 75% sequence identity, at least 80% sequence identity, at least 85% sequence identity, at least 90% sequence identity, at least 95% sequence identity, at least 97% sequence identity, at least 98% sequence identity, at least 99% sequence identity or 100% sequence identity to the mature polypeptide of SEQ ID NO: 2;

(b) a polypeptide encoded by a polynucleotide having at least 70% sequence identity, such as at least 75% sequence identity, at least 80% sequence identity, at least 85% sequence identity, at least 90% sequence identity, at least 95% sequence identity, at least 97% sequence identity, at least 98% sequence identity, at least 99% sequence identity or 100% sequence identity to the mature polypeptide coding sequence of SEQ ID NO: 1;

(c) a variant comprising a substitution, deletion, and/or insertion of one or more (several) amino acids of the mature polypeptide of SEQ ID NO: 2, wherein said variant having at least 70% sequence identity, such as at least 75% sequence identity, at least 80% sequence identity, at least 85% sequence identity, at least 90% sequence identity, at least 95% sequence identity, at least 97% sequence identity, at least 98% sequence identity, at least 99% sequence identity, but having less than 100% sequence identity to the mature polypeptide of SEQ ID NO 2; and (d) a fragment of a polypeptide of (a), (b) or (c) that has protease activity.

In one embodiment, the invention is directed to detergent compositions comprising an enzyme of the present invention in combination with one or more additional cleaning composition components, such as detergent components.

The choice of additional components is within the skill of the artisan and includes conventional ingredients, including the exemplary non-limiting components set forth below. The choice of components may include, for fabric care, the consideration of the type of fabric to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized.

When included therein the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein the detergent will usually contain from about 1% to about 40% by weight of a cationic surfactant. Non-limiting examples of cationic surfactants include alklydimethylehanolamine quat (ADMEAQ), cetyl-trimethylammonium bromide (CTAB), dimethyldistearylammonium chloride (DSDMAC), and alkylbenzyldimethylammonium, and combinations thereof, Alkyl quaternary ammonium compounds, Alkoxylated quaternary ammonium (AQA), When included therein the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamide (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein the detergent will usually contain from about 1% to about 40% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

When included therein the detergent will usually contain from about 1% to about 40% by weight of a zwitterionic surfactant. Non-limiting examples of zwitterionic surfactants include betaine, alkyldimethylbetaine, and sulfobetaine, and combinations thereof.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonates (STS), sodium xylene sulfonates (SXS), sodium cumene sulfonates (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65% by weight, such as about 5% to about 20% of a detergent builder or co-builder, or a mixture thereof. In a dish wash deteregent, the level of builder is typically 40-65%, particularly 50-65%. The builder and/or co-builder may particularly be a chelating agent that forms water-soluble complexes with Ca and Mg. Any builder and/or co-builder known in the art for use in laundry detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), iminodiethanol (DEA) and 2,2',2"-nitrilotriethanol (TEA), and carboxymethylinulin (CMI), and combinations thereof.

The detergent composition may also contain 0-40% by weight, such as about 1% to about 20%, of a detergent co-builder, or a mixture thereof. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), etheylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diylbis(phosphonic acid) (HEDP), ethylenediaminetetrakis(methylene)tetrakis(phosphonic acid) (EDTMPA), diethylenetriaminepentakis(methylene)pentakis(phosphonic acid) (DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl) aspartic acid (SEAS), N-(2-sulfomethyl) glutamic acid (SMGL), N-(2-sulfoethyl) glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(hydroxyethyl)-ethylidenediaminetriacetate (HEDTA), diethanolglycine (DEG), Diethylenetriamine Penta (Methylene Phosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053. Incrustation inhibitors such as phosphonates Bleaching Systems The detergent may contain 0-10% by weight, such as about 0.5% to about 5%, of a bleaching system. Any bleaching system known in the art for use in laundry detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. By Bleach activator is meant herein a compound which reacts with peroxygen bleach like hydrogen peroxide to form a Peracid. The peracid thus formed constitutes the activated bleach. Suitable bleach activators to be used herein include those belonging to the class of esters amides, imides or anhydrides, Suitable examples are tetracetyl ethylene diamine (TAED), sodium 3,5,5 trimethyl hexanoyloxybenzene sulphonat, diperoxy dodecanoic acid, 4-(dodecanoyloxy)benzenesulfonate (LOBS), 4-(decanoyloxy)benzenesulfonate, 4-(decanoyloxy)benzoate (DOBS), 4-(3,5,5-trimethylhexanoyloxyl) benzenesulfonate (ISONOBS), tetraacetylethylenediamine (TAED) and 4-(nonanoyloxy)benzenesulfonate (NOBS), and/or those disclosed in WO 98/17767. A particular family of bleach activators of interest was disclosed in EP624154 and particulary preferred in that family is acetyl triethyl citrate (ATC). ATC or a short chain triglyceride like Triacin has the advantage that it is environmental friendly as it eventually degrades into citric acid and alcohol. Furthermore acetyl triethyl citrate and triacetin has a good hydrolytical stability in the product upon storage and it is an efficient bleach activator. Finally ATC provides a good building capacity to the laundry additive. Alternatively, the bleaching system may comprise peroxyacids of, for example, the amide, imide, or sulfone type. The bleaching system may also comprise peracids such as 6-(phthaloylamino)percapronic acid (PAP). The bleaching system may also include a bleach catalyst. In some embodiments the bleach component may be an organic catalyst selected from the group consisting of organic catalysts having the following formulae:

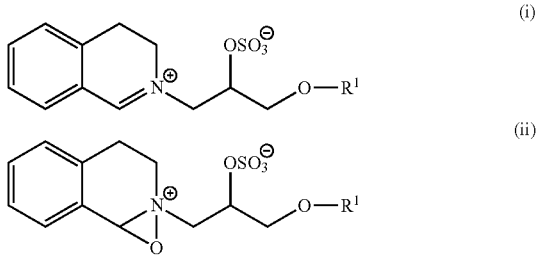

(iii) and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g., in WO2007/087258, WO2007/087244, WO2007/087259, WO2007/087242. Suitable photobleaches may for example be sulfonated zinc phthalocyanine Polymers The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of polyethylene terephthalate and polyoxyethene terephthalate (PET-POET), PVP, poly(vinylimidazole) (PVI), poly(vinylpyridin-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments which when formulated in detergent compositions can deposit onto a fabric when said fabric is contacted with wash liquor comprising said detergent compositions thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g., WO 2007/087257, WO2007/087243.

Additional Enzymes

The detergent additive as well as the detergent composition according to the invention may comprise one or more additional enzymes such as a protease, lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases:

Suitable cellulases include those of bacterial, fungal, plant, viral or animal origin e.g. vegetable or microbial origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include Celluzyme™, and Carezyme™ (Novozymes N5), Clazinase™, and Puradax HA™ (Genencor International Inc.), and KAC-500 (B)™ (Kao Corporation).

Proteases:

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family. In one aspect of the invention the additional protease may be a subtilase, such as a subtilisin or a variant hereof.

Examples of subtilisins are those derived from Bacillus such as subtilisin lentus, Bacillus lentus, subtilisin Novo, subtilisin Carlsberg, Bacillus licheniformis, subtilisin BPN', subtilisin 309, subtilisin 147 and subtilisin 168 described in WO 89/06279 and protease PD138 (WO 93/18140). Additional serine protease examples are described in WO 98/020115, WO 01/44452, WO 01/58275, WO 01/58276, WO 03/006602 and WO 04/099401. Further examples of subtilase variants may be those having mutations in any of the positions: 3, 4, 9, 15, 27, 36, 68, 76, 87, 95, 96, 97, 98, 99, 100, 101, 102, 103, 104, 106, 118, 120, 123, 128, 129, 130, 160, 167, 170, 194, 195, 199, 205, 217, 218, 222, 232, 235, 236, 245, 248, 252 and 274 using the BPN' numbering. More preferred the subtilase variants may comprise the mutations: S3T, V4I, S9R, A15T, K27R, *36D, V68A, N76D, N87S,R, *97E, A98S, S99G,D,A, S99AD, S101G, M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Examples of trypsin-like proteases are trypsin (e.g. of porcine or bovine origin) and the Fusarium protease described in WO 89/06270 and WO 94/25583. Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Examples of metalloproteases are the neutral metalloprotease as described in WO 07/044993 (Genencor Int.).

Preferred commercially available protease enzymes include Alcalase®, Coronase®, Duralase™, Durazym™, Esperase®, Everlase®, Kannase®, Liquanase®, Liquanase® Ultra, Ovozyme®, Polarzyme®, Primase®, Relase®, Savinase® and Savinase® Ultra, (Novozymes A/S), Axapee™ (Gist-Brocades N.V.), Excellase™, FN2™, FN3™, FN4™, Maxaca™, Maxapee™, Maxatase™, Properase™, Purafase™, Purafect™, Purafect OxP™, Purafect Prime and Puramax™ (DuPont/Genencor int.).

A further preferred protease is the alkaline protease from Bacillus lentus DSM 5483, as described for example in WO 95/23221, and variants thereof which are described in WO 92/21760, WO 95/23221, EP 1921147 and EP 1921148.

Lipases and Cutinases:

Suitable lipases and cutinases include those of bacterial, fungal, plant, viral or animal origin e.g. vegetable or microbial origin. Chemically modified or protein engineered mutants are included. Examples include lipase from Thermomyces, e.g., from T. lanuginosus (previously named Humicola lanuginosa) as described in EP 258 068 and EP 305 216, cutinase from Humicola, e.g. H. insolens as described in WO 96/13580, a Pseudomonas lipase, e.g., from P. alcaligenes or P. pseudoalcaligenes (EP 218 272), P. cepacia (EP 331 376), P. stutzeri (GB 1,372,034), P. fluorescens, Pseudomonas sp. strain SD 705 (WO 95/06720 and WO 96/27002), P. wisconsinensis (WO 96/12012), a Bacillus lipase, e.g., from B. subtilis (Dartois et al., 1993, Biochemica et Biophysica Acta, 1131: 253-360), B. stearothermophilus (JP 64/744992) or B. pumilus (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079, WO 97/07202, WO 00/060063, WO2007/087508 and WO 2009/109500.

Preferred commercially available lipase enzymes include Lipolase™, Lipolase Ultra™, and Lipex™; Lecitase™, Lipolex™; Lipoclean™, Lipoprime™ (Novozymes A/S). Other commercially available lipases include Lumafast (Genencor Int Inc); Lipomax (Gist-Brocades/Genencor Int Inc) and Bacillus sp lipase from Solvay.

Amylases:

Suitable amylases which can be used together with the protease of the invention may be an alpha-amylase or a glucoamylase and may be of bacterial or fungal origin. Chemically modified or protein engineered mutants are included. Amylases include, for example, alpha-amylases obtained from Bacillus, e.g., a special strain of Bacillus licheniformis, described in more detail in GB 1,296,839.

Suitable amylases include amylases having SEQ ID NO: 3 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from B. amyloliquefaciens shown in SEQ ID NO: 6 of WO 2006/066594 and residues 36-483 of the B. licheniformis alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from B. amyloliquefaciens shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476. More preferred variants are those having a deletion in positions 181 and 182 or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;

N128C+K178L+T182G+F202Y+Y305R+D319T+G475K;

S125A+N128C+K178L+T182G+Y305R+G475K; or

S125A+N128C+T131I+T165I+K178L+T182G+Y305R+G475K wherein the variants are C-terminally truncated and optionally further comprises a substitution at position 243 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, R446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO 2011/098531, WO 2013/001078 and WO 2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™ Purastar™, and Powerase (from Genencor International Inc.).

Peroxidases/Oxidases:

Suitable peroxidases/oxidases include those of bacterial, fungal, plant, viral or animal origin e.g. vegetable or microbial origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

Dispersants—

The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents—

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent—

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulphonic acid derivatives, diarylpyrazoline derivatives and bisphenyl-distyryl derivatives. Examples of the diaminostilbene-sulphonic acid derivative type of fluorescent whitening agents include the sodium salts of: 4,4'-bis-(2-diethanolamino-4-anilino-s-triazin-6-ylamino) stilbene-2,2'-disulphonate; 4,4'-bis-(2,4-dianilino-s-triazin-6-ylamino) stilbene-2,2'-disulphonate; 4,4'-bis-(2-anilino-4(N-methyl-N-2-hydroxy-ethylamino)-s-triazin-6-ylamino) stilbene-2,2'-disulphonate, 4,4'-bis-(4-phenyl-2,1,3-triazol-2-yl)stilbene-2,2'-disulphonate; 4,4'-bis-(2-anilino-4(1-methyl-2-hydroxy-ethylamino)-s-triazin-6-ylamino) stilbene-2,2'-disulphonate and 2-(stilbyl-4"-naptho-1,2':4,5)-1,2,3-trizole-2"-sulphonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4 anilino-s-triazin-6-ylamino) stilbene disulphonate. Tinopal CBS is the disodium salt of 2,2'-bis-(phenyl-styryl) disulphonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Soil Release Polymers—

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents—

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Detergent formulation forms: Layers (same or different phases), Pouches, versus forms for Machine dosing unit.

Pouches can be configured as single or multicompartments. It can be of any form, shape and material which are suitable for hold the composition, e.g. not allowing the release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxyprpyl methyl cellulose (HPMC). Preferably the level of polymer in the film for example PVA is at least about 60%. Preferred average molecular weight will typically be about 20,000 to about 150,000. Films can also be of blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticisers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids. Ref: (US2009/0011970 A1).

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may be non-aqueous.

Laundry Soap Bars

The proteases of the invention may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g. a two stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix containing soap, an enzyme, optionally one or more additional enzymes, a protease inhibitor, and a salt of a monovalent cation and an organic anion may be prepared and the mixture is then plodded. The enzyme and optional additional enzymes may be added at the same time as the protease inhibitor for example in liquid form. Besides the mixing step and the plodding step, the process may further comprise the steps of milling, extruding, cutting, stamping, cooling and/or wrapping.

Granular Detergent Formulations

A granular detergent may be formulated as described in WO09/092699, EP1705241, EP1382668, WO07/001262, U.S. Pat. No. 6,472,364, WO04/074419 or WO09/102854. Other useful detergent formulations are described in WO09/124162, WO09/124163, WO09/117340, WO09/117341, WO09/117342, WO09/072069, WO09/063355, WO09/132870, WO09/121757, WO09/112296, WO09/112298, WO09/103822, WO09/087033, WO09/050026, WO09/047125, WO09/047126, WO09/047127, WO09/047128, WO09/021784, WO09/010375, WO09/000605, WO09/122125, WO09/095645, WO09/040544, WO09/040545, WO09/024780, WO09/004295, WO09/004294, WO09/121725, WO09/115391, WO09/115392, WO09/074398, WO09/074403, WO09/068501, WO09/065770, WO09/021813, WO09/030632, and WO09/015951.

WO2011025615, WO2011016958, WO2011005803, WO2011005623, WO2011005730, WO2011005844, WO2011005904, WO2011005630, WO2011005830, WO2011005912, WO2011005905, WO2011005910, WO2011005813, WO2010135238, WO2010120863, WO2010108002, WO2010111365, WO2010108000, WO2010107635, WO2010090915, WO2010033976, WO2010033746, WO2010033747, WO2010033897, WO2010033979, WO2010030540, WO2010030541, WO2010030539, WO2010024467, WO2010024469, WO2010024470, WO2010025161, WO2010014395, WO2010044905,

WO2010145887, WO2010142503, WO2010122051, WO2010102861, WO2010099997, WO2010084039, WO2010076292, WO2010069742, WO2010069718, WO2010069957, WO2010057784, WO2010054986, WO2010018043, WO2010003783, WO2010003792,

WO2011023716, WO2010142539, WO2010118959, WO2010115813, WO2010105942, WO2010105961, WO2010105962, WO2010094356, WO2010084203, WO2010078979, WO2010072456, WO2010069905, WO2010076165, WO2010072603, WO2010066486, WO2010066631, WO2010066632, WO2010063689, WO2010060821, WO2010049187, WO2010031607, WO2010000636.

Uses

The present invention is also directed to methods for using the protease according to the invention or compositions thereof in cleaning processes such as in laundry of textiles and fabrics, such as house hold laundry washing and industrial laundry washing.

The invention is also directed to methods for using the compositions thereof in hard surface cleaning such as automated Dish Washing (ADW), car wash and cleaning of Industrial surfaces. Thus one embodiment, the present invention relates to the use in cleaning such as laundry or dish wash of a protease according to the invention or a detergent composition comprising a protease according to the present invention having a sequence identity to the mature polypeptide of SEQ ID NO 2 of at least 60%. Thus in one embodiment, the present invention relates to the use in a detergent, a cleaning process and/or laundry process of a polypeptide having a sequence identity to the mature polypeptide of SEQ ID NO: 2 of at least 70%, at least 71%, at least 72%, at least 73%, at least 74%, at least 75%, at least 76%, at least 77%, at least 78%, at least 79% at least 80% at least 81% at least 82% at least 83% at least 84%, at least 85%, at least 86%, at least 87%, at least 88%, at least 89% at least 90%, at least 91%, at least 92%, at least 93%, at least 94%, at least 95%, at least 96%, at least 97%, at least 98%, at least 99%, or 100% sequence identity to the mature polypeptide of SEQ ID NO 2 and which have protease activity.

The polypeptides of the present invention may be added to and thus become a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising a polypeptide of the present invention as described herein.

The soils and stains that are important for detergent formulators are composed of many different substances, and a range of different enzymes, all with different substrate specificities have been developed for use in detergents both in relation to laundry and hard surface cleaning, such as dishwashing. These enzymes are considered to provide an enzyme detergency benefit, since they specifically improve stain removal in the cleaning process they are applied in as compared to the same process without enzymes. Stain removing enzymes that are known in the art include enzymes such as carbohydrases, amylases, proteases, lipases, cellulases, hemicellulases, xylanases, cutinases, and pectinase.

In one aspect, the present invention concerns the use of a polypeptide having a sequence identity to the mature polypeptide of SEQ ID NO: 2 of at least 70%, at least 71%, at least 72%, at least 73%, at least 74%, at least 75%, at least 76%, at least 77%, at least 78%, at least 79% at least 80% at least 81% at least 82% at least 83% at least 84%, at least 85%, at least 86%, at least 87%, at least 88%, at least 89% at least 90%, at least 91%, at least 92%, at least 93%, at least 94%, at least 95%, at least 96%, at least 97%, at least 98%, at least 99%, or 100% sequence identity to the mature polypeptide of SEQ ID NO 2 in detergent compositions and cleaning processes, such as laundry and hard surface cleaning. Thus, in one aspect, the present invention demonstrates the detergency effect of the protease according to the invention on various stains and under various conditions. In a particular aspect of the invention the detergent composition and the use in cleaning process concerns the use of a protease of the invention together with at least one of the above mentioned stain removal enzymes.

In a preferred aspect of the present invention, the protease of the invention may be combined with at least two enzymes. These additional enzymes are described in details in the section "additonal enzymes"; more preferred at least three, four or five enzymes. Preferably, the enzymes have different substrate specificity, e.g., carbolytic activity, proteolytic activity, amylolytic activity, lipolytic activity, hemicellulytic activity or pectolytic activity. The enzyme combination may for example be a protease of the invention with another stain removing enzyme, e.g., a protease of the invention and an amylase, a protease of the invention and a cellulase, a protease of the invention and a hemicellulase, a protease of the invention and a lipase, a protease of the invention and a cutinase, a protease of the invention and a pectinase or a protease of the invention and an anti-redeposition enzyme. More preferably, the protease of the invention is combined with at least two other stain removing enzymes, e.g., a protease of the invention, a lipase and an amylase; or a protease of the invention, an amylase and a pectinase; or a protease of the invention, an amylase and a cutinase; or a protease of the invention, an amylase and a cellulase; or a protease of the invention, an amylase and a hemicellulase; or a protease of the invention, a lipase and a pectinase; or a protease of the invention, a lipase and a cutinase; or a protease of the invention, a lipase and a cellulase; or a protease of the invention, a lipase and a hemicellulase. Even more preferably, a protease of the invention may be combined with at least three other stain removing enzymes, e.g., a protease of the invention, an amylase, a lipase and a pectinase; or a protease of the invention, an amylase, a lipase and a cutinase; or a protease of the invention, an amylase, a lipase and a cellulase; or a protease of the invention, an amylase, a lipase and a hemicellulase. A protease of the invention may be combined with any of the enzymes selected from the non-exhaustive list comprising: carbohydrases, such as an amylase, a hemicellulase, a pectinase, a cellulase, a xanthanase or a pullulanase, a peptidase, other proteases or a lipase.

In another embodiment of the present invention, a protease of the invention may be combined with one or more metalloproteases, such as a M4 Metalloprotease, including Neutrase™ or Thermolysin. Such combinations may further comprise combinations of the other detergent enzymes as outlined above.

The cleaning process or the textile care process may for example be a laundry process, a dishwashing process or cleaning of hard surfaces such as bathroom tiles, floors, table tops, drains, sinks and washbasins. Laundry processes can for example be household laundering, but it may also be industrial laundering. Furthermore, the invention relates to a process for laundering of fabrics and/or garments where the process comprises treating fabrics with a washing solution containing a detergent composition, and at least one protease of the invention. The cleaning process or a textile care process can for example be carried out in a machine washing process or in a manual washing process. The washing solution can for example be an aqueous washing solution containing a detergent composition.

The fabrics and/or garments subjected to a washing, cleaning or textile care process of the present invention may be conventional washable laundry, for example household laundry. Preferably, the major part of the laundry is garments and fabrics, including knits, woven, denims, non-woven, felts, yarns, and towelling. The fabrics may be cellulose based such as natural cellulosics, including cotton, flax, linen, jute, ramie, sisal or coir or manmade cellulosics (e.g., originating from wood pulp) including viscose/rayon, ramie, cellulose acetate fibers (tricell), lyocell or blends thereof. The fabrics may also be non-cellulose based such as natural polyamides including wool, camel, cashmere, mohair, rabit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g., polyamide fibers, acrylic fibers, polyester fibers, polyvinyl alcohol fibers, polyvinyl chloride fibers, polyurethane fibers, polyurea fibers, aramid fibers), and cellulose-containing fibers (e.g., rayon/viscose, ramie, flax, linen, jute, cellulose acetate fibers, lyocell).

The last few years there has been an increasing interest in replacing components in detergents, which is derived from petrochemicals with renewable biological components such as enzymes and polypeptides without compromising the wash performance. When the components of detergent compositions change new enzyme activities or new enzymes having alternative and/or improved properties compared to the common used detergent enzymes such as proteases, lipases and amylases is needed to achieve a similar or improved wash performance when compared to the traditional detergent compositions.

The invention further concerns the use of a protease of the invention in a proteinaceous stain removing processes. The proteinaceous stains may be stains such as food stains, e.g., baby food, sebum, cocoa, egg, blood, milk, ink, grass, or a combination hereof.

Typical detergent compositions includes various components in addition to the enzymes, these components have different effects, some components like the surfactants lower the surface tension in the detergent, which allows the stain being cleaned to be lifted and dispersed and then washed away, other components like bleach systems removes discolor often by oxidation and many bleaches also have strong bactericidal properties, and are used for disinfecting and sterilizing. Yet other components like builder and chelator softens, e.g., the wash water by removing the metal ions form the liquid.

In a particular embodiment, the invention concerns the use of a composition comprising a protease of the invention, wherein said enzyme composition further comprises at least one or more of the following a surfactant, a builder, a chelator or chelating agent, bleach system or bleach component in laundry or dish wash.

In a preferred embodiment of the invention, the amount of a surfactant, a builder, a chelator or chelating agent, bleach system and/or bleach component are reduced compared to amount of surfactant, builder, chelator or chelating agent, bleach system and/or bleach component used without the added protease of the invention. Preferably the at least one component which is a surfactant, a builder, a chelator or chelating agent, bleach system and/or bleach component is present in an amount that is 1% less, such as 2% less, such as 3% less, such as 4% less, such as 5% less, such as 6% less, such as 7% less, such as 8% less, such as 9% less, such as 10% less, such as 15% less, such as 20% less, such as 25% less, such as 30% less, such as 35% less, such as 40% less, such as 45% less, such as 50% less than the amount of the component in the system without the addition of protease of the invention, such as a conventional amount of such component. In one aspect, the protease of the invention is used in detergent compositions wherein said composition is free of at least one component which is a surfactant, a builder, a chelator or chelating agent, bleach system or bleach component and/or polymer.

Thus, one aspect the invention relates to the use of a detergent composition comprising one or more detergent components and a polypeptide having protease activity wherein the polypeptide having protease activity is selected among:
  a) a polypeptide having at least 70% sequence identity, such as at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2;
  (b) a polypeptide encoded by a polynucleotide that hybridizes under high stringency conditions, or very high stringency conditions with
     (i) the mature polypeptide coding sequence of SEQ ID NO: 1;
     (ii) the full-length complementary strand of (i);
  (c) a polypeptide encoded by a polynucleotide having at least 70% sequence identity, such as at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1; and/or
  (d) a variant comprising a substitution, deletion, and/or insertion of one or more (several) amino acids of the mature polypeptide of SEQ ID NO: 2, wherein said variant having at least at least 70% sequence identity, such as at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but having less than 100% sequence identity to the mature polypeptide of SEQ ID NO 2; and
  (e) a fragment of a polypeptide of (a), (b), (c) or (d), which has protease activity in a cleaning processes such as laundry and hard surface cleaning such as dish wash.

Washing Method

The detergent compositions of the present invention are ideally suited for use in laundry applications. Accordingly, the present invention includes a method for laundering a fabric. The method comprises the steps of contacting a fabric to be laundered with a cleaning laundry solution comprising the detergent composition according to the invention. The fabric may comprise any fabric capable of being laundered in normal consumer use conditions. The solution preferably has a pH of from about 5.5 to about 11. The compositions may be employed at concentrations of from about 100 ppm, preferably 500 ppm to about 15,000 ppm in solution. The water temperatures typically range from about 5° C. to about 90° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

In particular embodiments, the washing method is conducted at a pH of from about 5.0 to about 11.5, or in alternative embodiments, even from about 6 to about 10.5, such as about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5. to about 7, about 6 to about 11, about 6 to about 10, about 6 to about 9, about 6 to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, preferably about 5.5 to about 9, and more preferably about 6 to about 8.

In particular embodiments, the washing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, about 30° dH. Under typical European wash conditions, the degree of hardness is about 15° dH, under typical US wash conditions about 6° dH, and under typical Asian wash conditions, about 3° dH.

The present invention relates to a method of cleaning a fabric, a dishware or hard surface with a detergent composition comprising a protease of the invention.

A preferred embodiment concerns a method of cleaning, said method comprising the steps of: contacting an object with a cleaning composition comprising a protease of the invention under conditions suitable for cleaning said object. In a preferred embodiment the cleaning composition is a detergent composition and the process is a laundry or a dish wash process.

Still another embodiment relates to a method for removing stains from fabric which comprises contacting said a fabric with a composition comprising a protease of the invention under conditions suitable for cleaning said object.

In a preferred embodiment, the compositions for use in the methods above further comprises at least one additional enzyme as set forth in the "additional enzymes" section above, such as an enzyme selected from the group consisting of carbohydrases, peptidases, proteases, lipases, cellulase, xylanases or cutinases or a combination hereof. In yet another preferred embodiment the compositions comprises a reduced amount of at least one or more of the following components a surfactant, a builder, a chelator or chelating agent, bleach system or bleach component or a polymer.

Also contemplated are compositions and methods of treating fabrics (e.g., to desize a textile) using one or more of the protease of the invention. The protease can be used in any fabric-treating method which is well known in the art (see, e.g., U.S. Pat. No. 6,077,316). For example, in one aspect, the feel and appearance of a fabric is improved by a method comprising contacting the fabric with a protease in a solution. In one aspect, the fabric is treated with the solution under pressure.

In one embodiment, the protease is applied during or after the weaving of textiles, or during the desizing stage, or one or more additional fabric processing steps. During the weaving of textiles, the threads are exposed to considerable mechanical strain. Prior to weaving on mechanical looms, warp yarns are often coated with sizing starch or starch derivatives in order to increase their tensile strength and to prevent breaking. The protease can be applied to remove these sizing protein or protein derivatives. After the textiles have been woven, a fabric can proceed to a desizing stage. This can be followed by one or more additional fabric processing steps. Desizing is the act of removing size from textiles. After weaving, the size coating should be removed before further processing the fabric in order to ensure a homogeneous and wash-proof result. Also provided is a method of desizing comprising enzymatic hydrolysis of the size by the action of an enzyme.

Thus, in one aspect the invention relates to the use in a cleaning process such as laundry or dish wash e.g. manual or automated of a polypeptide having protease activity selected among:
a) a polypeptide having at least 70% sequence identity, such as at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2;
(b) a polypeptide encoded by a polynucleotide that hybridizes under high stringency conditions, or very high stringency conditions with
(i) the mature polypeptide coding sequence of SEQ ID NO: 1;
(ii) the full-length complementary strand of (i);
(c) a polypeptide encoded by a polynucleotide having at least 70% sequence identity, such as at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1,
(d) a variant comprising a substitution, deletion, and/or insertion of one or more (several) amino acids of the mature polypeptide of SEQ ID NO: 2, wherein said variant having at least at least 70% sequence identity, such as at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but having less than 100% sequence identity to the mature polypeptide of SEQ ID NO 2; and/or
(e) a fragment of a polypeptide of (a), (b), (c) or (d), which has protease activity.

The invention further relates to a method for degrading or removing proteinaceous materials from a textile or a hard surface comprising treating the textile or the hard surface with a detergent composition comprising one or more detergent component and a polypeptide having protease activity selected among:
a) a polypeptide having at least 70% sequence identity, such as at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2;
(b) a polypeptide encoded by a polynucleotide that hybridizes under high stringency conditions, or very high stringency conditions with
(i) the mature polypeptide coding sequence of SEQ ID NO: 1;
(ii) the full-length complementary strand of (i);
(c) a polypeptide encoded by a polynucleotide having at least 70% sequence identity, such as at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1;

(d) a variant comprising a substitution, deletion, and/or insertion of one or more (several) amino acids of the mature polypeptide of SEQ ID NO: 2, wherein said variant having at least at least 70% sequence identity, such as at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but having less than 100% sequence identity to the mature polypeptide of SEQ ID NO 2; and/or (e) a fragment of a polypeptide of (a), (b), (c) or (d), which has protease activity.

Low Temperature Uses

One embodiment of the invention concerns a method of doing laundry, dish wash or industrial cleaning comprising contacting a surface to be cleaned with a protease of the invention, and wherein said laundry, dish wash, industrial or institutional cleaning is performed at a temperature of about 40° C. or below. One embodiment of the invention relates to the use of a protease of the invention in laundry, dish wash or a cleaning process wherein the temperature in laundry, dish wash, industrial cleaning is about 40° C. or below.

In another embodiment, the invention concerns the use of a protease of the invention in a protein removing process, wherein the temperature in the protein removing process is about 40° C. or below.

The present invention also relates to the use in laundry, dish wash or industrial cleaning process of a protease of the invention having at least one improved property compared to a reference protease and wherein the temperature in laundry, dish wash or cleaning process is performed at a temperature of about 40° C. or below.

In each of the above-identified methods and uses, the wash temperature is about 40° C. or below, such as about 39° C. or below, such as about 38° C. or below, such as about 37° C. or below, such as about 36° C. or below, such as about 35° C. or below, such as about 34° C. or below, such as about 33° C. or below, such as about 32° C. or below, such as about 31° C. or below, such as about 30° C. or below, such as about 29° C. or below, such as about 28° C. or below, such as about 27° C. or below, such as about 26° C. or below, such as about 25° C. or below, such as about 24° C. or below, such as about 23° C. or below, such as about 22° C. or below, such as about 21° C. or below, such as about 20° C. or below, such as about 19° C. or below, such as about 18° C. or below, such as about 17° C. or below, such as about 16° C. or below, such as about 15° C. or below, such as about 14° C. or below, such as about 13° C. or below, such as about 12° C. or below, such as about 11° C. or below, such as about 10° C. or below, such as about 9° C. or below, such as about 8° C. or below, such as about 7° C. or below, such as about 6° C. or below, such as about 5° C. or below, such as about 4° C. or below, such as about 3° C. or below, such as about 2° C. or below, such as about 1° C. or below.

In another preferred embodiment, the wash temperature is in the range of about 5-40° C., such as about 5-30° C., about 5-20° C., about 5-10° C., about 10-40° C., about 10-30° C., about 10-20° C., about 15-40° C., about 15-30° C., about 15-20° C., about 20-40° C., about 20-30° C., about 25-40° C., about 25-30° C., or about 30-40° C. In a particular preferred embodiment the wash temperature is about 30° C.

In particular embodiments, the low temperature washing method is conducted at a pH of from about 5.0 to about 11.5, or in alternative embodiments, even from about 6 to about 10.5, such as about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5. to about 7, about 6 to about 11, about 6 to about 10, about 6 to about 9, about 6 to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, preferably about 5.5 to about 9, and more preferably about 6 to about 9.

In particular embodiments, the low temperature washing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, about 30° dH. Under typical European wash conditions, the degree of hardness is about 15° dH, under typical US wash conditions about 6° dH, and under typical Asian wash conditions, about 3° dH.

EXAMPLES

Materials and Methods

LB Skim Milk Agar

LB skim milk agar was made by mixing 37 g dehydrate LB agar medium (Sigma L3027) with 20 ml Skim milk (Arla, Denmark) and adjusting the total volume to 1000 ml. The mixture was subsequently sterilized by autoclaving 121C for 16 min.

Wash Assays

Automatic Mechanical Stress Assay (AMSA) for Laundry

In order to assess the wash performance in laundry washing experiments are performed, using the Automatic Mechanical Stress Assay (AMSA). With the AMSA, the wash performance of a large quantity of small volume enzyme-detergent solutions can be examined. The AMSA plate has a number of slots for test solutions and a lid firmly squeezing the laundry sample, the textile to be washed against all the slot openings. During the washing time, the plate, test solutions, textile and lid are vigorously shaken to bring the test solution in contact with the textile and apply mechanical stress in a regular, periodic oscillating manner. For further description see WO02/42740 especially the paragraph "Special method embodiments" at page 23-24.

The wash performance is measured as the brightness of the colour of the textile washed. Brightness can also be expressed as the intensity of the light reflected from the sample when illuminated with white light. When the sample is stained the intensity of the reflected light is lower, than that of a clean sample. Therefore the intensity of the reflected light can be used to measure wash performance.

Colour measurements are made with a professional flat-bed scanner (Kodak iQsmart, Kodak, Midtager 29, DK-2605 Brøndby, Denmark), which is used to capture an image of the washed textile.

To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$Int = \sqrt{r^2 + g^2 + b^2}.$$

TABLE 1

Composition of model detergents and test materials

| | |
|---|---|
| Laundry powder model detergent A | Sodium citrate dihydrate 32.3% |
| | Sodium-LAS 24.2% |
| | Sodium lauryl sulfate 32.2% |
| | Neodol 25-7 (alcohol ethoxylate) 6.4% |
| | Sodium sulfate 4.9% |
| Laundry liquid model detergent B | Water 30.63% |
| | Sodium hydroxide 2.95% |
| | Dodecylbenzensulfonic acid 11.52% |
| | Fatty acids (Soya) 5.50% |
| | Propane-1,2-diol (MPG) 5.05% |
| | Water 17.38% |
| | C13-alcohol ethoxylate, 10.50% |
| | Diethylenetriaminepentakis (methylenephosphonic acid) (DTMPA) 3.08% |
| | Triethanolamine (TEA) 2.22% |
| | Fatty acids (Coco) 4.50% |
| | Sodium citrate monohydrate 1.00% |
| | Ethanol 4.63% |
| | Syntran 5909 (opacifier) 0.30% |
| | Perfume 0.35% |
| Test material | PC-03 (Chocolate-milk/ink on cotton/polyester) |
| | C-10 (Oil/milk/pigment on cotton) |
| | PC-05 (Blood/milk/ink on cotton/polyester) |
| | EMPA117EH (Blood/milk/ink on cotton/polyester) |
| | CS-37, Full egg with pigment non-aged on cotton |

Test materials are obtained from Center for Testmaterials BV, P.O. Box 120, 3133 KT Vlaardingen, the Netherlands and EMPA Testmaterials AG, Movenstrasse 12, CH-9015 St. Gallen, Switzerland.

Protease Assays

1) Suc-AAPF-pNA Assay:

pNA substrate: Suc-AAPF-pNA (Bachem L-1400).
Temperature: Room temperature (25° C.)
Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 3.0, 4.0, 5.0, 6.0, 7.0, 8.0, 9.0, 10.0, and 11.0 with HCl or NaOH.
20 µl protease (diluted in 0.01% Triton X-100) was mixed with 100 µl assay buffer. The assay was started by adding 100 µl pNA substrate (50 mg dissolved in 1.0 µl DMSO and further diluted 45× with 0.01% Triton X-100). The increase in $OD_{405}$ was monitored as a measure of the protease activity.

2) Protazyme AK Assay:

Substrate: Protazyme AK tablet (cross-linked and dyed casein; from Megazyme)
Temperature: controlled (assay temperature).
Assay buffer: 100 mM succinic acid, 100 mM HEPES, 100 mM CHES, 100 mM CABS, 1 mM $CaCl_2$, 150 mM KCl, 0.01% Triton X-100, pH 6.5 or pH 7.0.
A Protazyme AK tablet was suspended in 2.0 ml 0.01% Triton X-100 by gentle stirring. 500 µl of this suspension and 500 µl assay buffer were dispensed in an Eppendorf tube and placed on ice. 20 µl protease sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm.). The incubation was stopped by transferring the tube back to the ice bath. Then the tube was centrifuged in an ice cold centrifuge for a few minutes and 200 µl supernatant was transferred to a microtiter plate. $OD_{650}$ was read as a measure of protease activity. A buffer blind was included in the assay (instead of enzyme).

3) Suc-AAPX-pNA Assay:

pNA substrates: Suc-AAPA-pNA (Bachem L-1775)
    Suc-AAPR-pNA (Bachem L-1720)
    Suc-AAPD-pNA (Bachem L-1835)
    Suc-AAPI-pNA (Bachem L-1790)
    Suc-AAPM-pNA (Bachem L-1395)
    Suc-AAPV-pNA (Bachem L-1770)
    Suc-AAPL-pNA (Bachem L-1390)
    Suc-AAPE-pNA (Bachem L-1710)
    Suc-AAPK-pNA (Bachem L-1725)
    Suc-AAPF-pNA (Bachem L-1400)
Temperature: Room temperature (25° C.)
Assay buffer: 100 mM succinic acid, 100 mM HEPES, 100 mM CHES, 100 mM CABS, 1 mM $CaCl_2$, 150 mM KCl, 0.01% Triton X-100, pH 9.0.
20 µl protease (diluted in 0.01% Triton X-100) was mixed with 100 µl assay buffer. The assay was started by adding 100 µl pNA substrate (50 mg dissolved in 1.0 µl DMSO and further diluted 45× with 0.01% Triton X-100). The increase in $OD_{405}$ was monitored as a measure of the protease activity.

Example 1. Design of Optimized DNA Sequence

The sequence of a family S8 protease derived from a strain belonging to the genus *Streptomyces* was identified in a public database having the accession number SWISSPROT:DIXSD4. In order to express the protease a gene encoding the protease with a codon usage optimized for expression in a *Bacillus* strain was designed, having the sequence shown in SEQ ID NO: 1. The codon optimization process is a method known in the art and is also described in WO 2012025577.

Example 2. Expression of the Protease

A DNA fragment having the sequence of SEQ ID NO: 1 was synthetized (Geneart®, Life Technologies, Naerum, Denmark) and cloned into a *Bacillus subtilis* expression vector according to the procedure described in WO 2012025577. The synthetic protease gene was expressed under control of a triple promoter system consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The expression cassette has also been described in WO 99/43835. The resulting plasmid denoted C362T was transformed into a protease deficient *Bacillus subtilis* expression strain and plated on LB+6 mg/l CAM.

Transformants were streaked on LB+CAM+skimmed milk plates, incubated over night at 37° C. Transformants expressing the polypeptide having protease activity showed clearing zones around the colonies indicating the presence of proteolytic activity.

A transformant expressing the protease as indicated by clearing zones on skimmed milk plates was grown in rich liquid medium at 37° C. and shaking 225 rpm for 5 days. The supernatant was separated from the cells by centrifugation at 10000 rpm for 30 minutes followed by filtration through a 0.45 µm filter. The supernatant was stored at −20° C. until use.

40 µl thawed sample was added 10 µl 50% trichloro acetic acid (TCA) and incubated on ice for 5 minutes before centrifugating 40000 rpm for 5 minutes. The supernatant was removed and 20 µl SDS-PAGE sample buffer (Nupage, Invitrogen) was added to the pellet followed by pipetting up and down until the pellet was completely dissolved.

The sample was heated at 99 C for 3 minutes and loaded on a 8-16% Crition Stainfree SDS-PAGE gel (Biorad) and run in a tris-glycin buffer according to the manufacturer's instructions. The gel was developed in a Criterion Stain Free Imager (Biorad) according to the manufacturer's instructions.

A clear band on approximately 40 kDa was seen in the transformant sample representing the expressed protease.

Example 3. Purification of the S8 Protease from *Streptomyces* sp. ACTE

The culture supernatant from example 2 was thawed, centrifuged (20000×g, 20 min) and the supernatant was carefully decanted from the precipitate. The supernatant was filtered through a Nalgene 0.2 μm filtration unit in order to remove the rest of the *Bacillus* host cells. Solid ammonium sulphate was added to the 0.2 μm filtrate to a final concentration of 1.6M $(NH_4)_2SO_4$ and the solution were stirred for 20 minutes at room temperature to ensure equilibration. The protease solution was applied to a Phenyl-sepharose FF (high substitution, from GE Healthcare) column equilibrated in 20 mM HEPES/NaOH, 2 mM $CaCl_2$, 1.6M $(NH_4)_2SO_4$, pH 8.0. After washing the column extensively with the equilibration buffer, the protease was eluted with a linear gradient over three column volumes between the equilibration buffer and 20 mM HEPES/NaOH, 2 mM $CaCl_2$, pH 8.0 with 25% (v/v) isopropanol. Fractions from the column were tested for protease activity (using the Suc-AAPF-pNA assay at pH 9) and the protease peak was pooled. The pool was transferred to 20 mM $CH_3COOH$/NaOH, 2 mM $CaCl_2$, pH 5.0 on a G25 sephadex column and the G25 sephadex transferred enzyme was diluted with deionized water to give a conductivity of 1.2 mS/cm. The adjusted protease solution was applied to a SOURCE 30S column (from GE Healthcare) equilibrated in 20 mM $CH_3COOH$/NaOH, 2 mM $CaCl_2$, pH 5.0. After washing the column extensively with the equilibration buffer, the protease was eluted with a linear NaCl gradient (0→0.5M) in the same buffer over eight column volumes. Fractions from the column were analyzed for protease activity (using the Suc-AAPF-pNA assay at pH 9) and peak-fractions were further analyzed by SDS-PAGE. Fractions, with a major band at approx. 31 kDa on the coomassie stained SDS-PAGE gel, were pooled and were used for further characterization.

Example 4. Characterization of the S8 Protease from *Streptomyces* sp. ACTE

The Suc-AAPF-pNA assay was used for obtaining the pH-activity profile and the pH-stability profile (residual activity after 2 hours at indicated pH-values). For the pH-stability profile the protease was diluted 10× in the different Assay buffers to reach the pH-values of these buffers and then incubated for 2 hours at 37° C. After incubation, the pH of the protease incubations was transferred to the same pH-value, before assay for residual activity, by dilution in the pH 9.0 Assay buffer. The Protazyme AK assay was used for obtaining the temperature-activity profile at pH 7.0 (The Protazyme AK assay was used for obtaining the temperature-activity profile for Savinase (SEQ ID NO 3) at pH 9.0). The Suc-AAPF-pNA assay and ten different Suc-AAPX-pNA substrates were used for obtaining the P1-specificity of the enzymes at pH 9.0.

The results are shown in Tables 2-5 below. For Table 2, the activities are relative to the optimal pH for the enzyme. For Table 3, the activities are residual activities relative to a sample, which was kept at stable conditions (5° C., pH 9.0). For Table 4, the activities are relative to the optimal temperature at pH 7.0 for the enzyme. For Table 5, the activities are relative to the best substrate (Suc-AAPF-pNA) for the enzyme.

TABLE 2 pH-activity profile

| pH | *Streptomyces* sp. ACTE S8 protease | Savinase |
|---|---|---|
| 2 | 0.00 | 0.00 |
| 3 | 0.00 | 0.00 |
| 4 | 0.00 | 0.00 |
| 5 | 0.04 | 0.01 |
| 6 | 0.27 | 0.05 |
| 7 | 0.75 | 0.33 |
| 8 | 1.00 | 0.85 |
| 9 | 0.93 | 1.00 |
| 10 | 0.96 | 0.91 |
| 11 | 0.97 | 0.77 |

TABLE 3 pH-stability profile (residual activity after 2 hours at 37° C.)

| pH | *Streptomyces* sp. ACTE S8 protease | Savinase |
|---|---|---|
| 2 | 0.00 | 0.00 |
| 3 | 0.00 | 0.00 |
| 4 | 0.96 | 0.16 |
| 5 | 1.00 | 0.97 |
| 6 | 1.00 | 1.02 |
| 7 | 1.01 | 1.00 |
| 8 | 0.98 | 0.95 |
| 9 | 0.94 | 0.95 |
| 10 | 1.10 | 0.97 |
| 11 | 1.04 | 0.98 |
| After 2 hours at 5° C. | 1.00 (at pH 9) | 1.00 (at pH 9) |

TABLE 4

Temperature activity profile at pH 7.0 or pH 9.0

| Temp (° C.) | *Streptomyces* sp. ACTE S8 protease (pH 7) | Savinase (pH 9) |
|---|---|---|
| 15 | 0.00 | 0.02 |
| 25 | 0.03 | 0.04 |
| 37 | 0.03 | 0.06 |
| 50 | 0.13 | 0.19 |
| 60 | 0.31 | 0.42 |
| 70 | 0.66 | 1.00 |
| 80 | 1.00 | 0.63 |
| 90 | 0.36 | 0.25 |

TABLE 5

P1-specificity on 10 Suc-AAPX-pNA substrates at pH 9.0

| Suc-AAPX-pNA | *Streptomyces* sp. ACTE S8 protease | Savinase |
|---|---|---|
| Suc-AAPA-pNA | 0.04 | 0.10 |
| Suc-AAPR-pNA | 0.01 | 0.00 |
| Suc-AAPD-pNA | 0.00 | 0.00 |
| Suc-AAPI-pNA | 0.00 | 0.00 |
| Suc-AAPM-pNA | 0.40 | 0.92 |
| Suc-AAPV-pNA | 0.00 | 0.00 |
| Suc-AAPL-pNA | 0.20 | 0.18 |
| Suc-AAPE-pNA | 0.00 | 0.01 |
| Suc-AAPK-pNA | 0.00 | 0.01 |
| Suc-AAPF-pNA | 1.00 | 1.00 |

Figure 2:
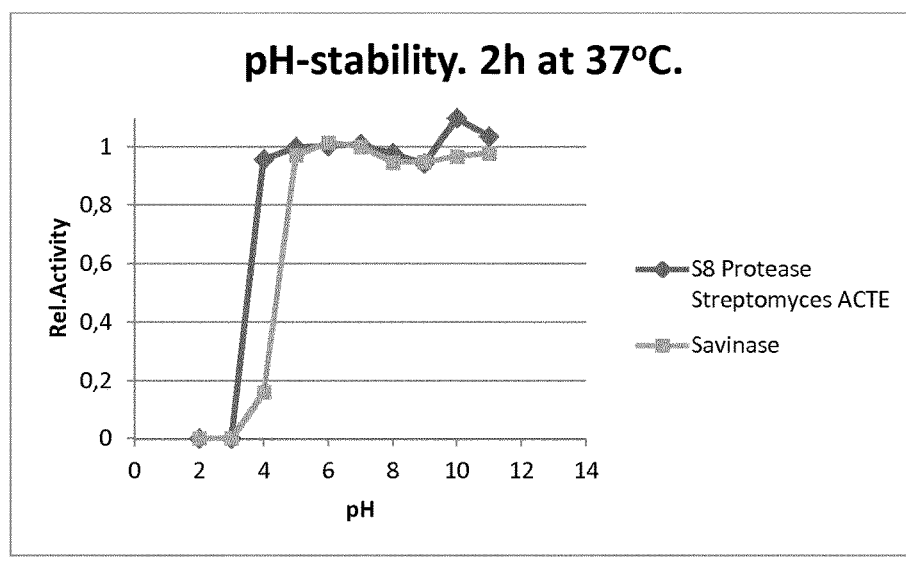
FIG. 2 shows the pH-stability (residual activity after 2 hours at 37° C.).
Figure 3:
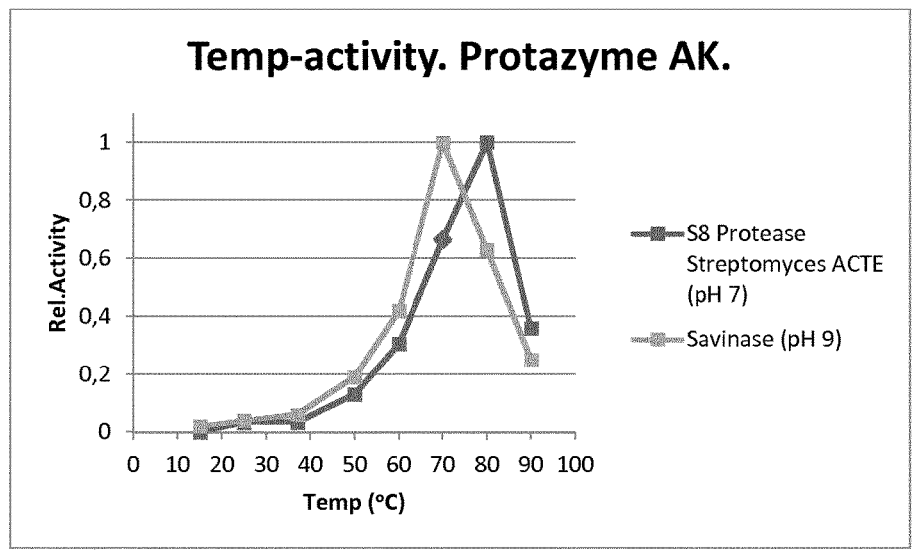
FIG. 3 shows the temperature-activity on Protazyme AK substrate.
Figure 4:
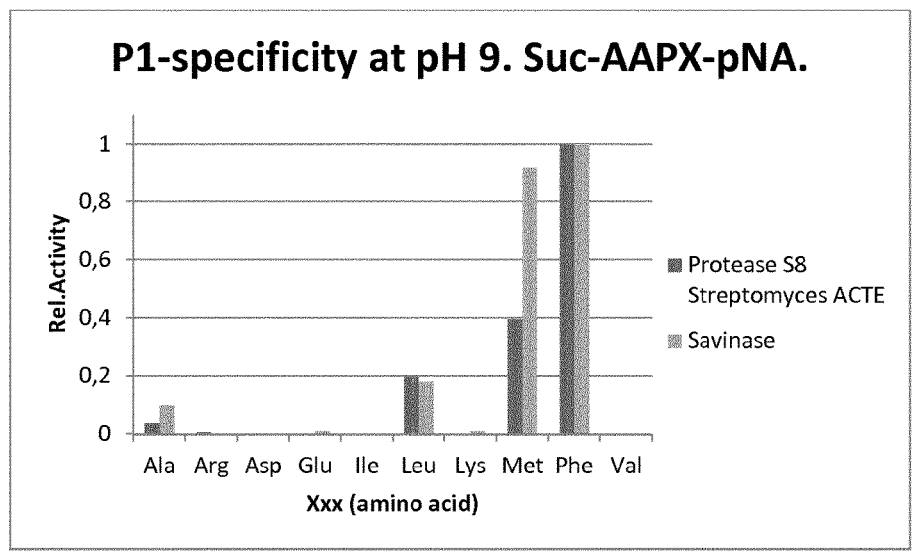
FIG. 4 shows the specificity on Suc-AAPX-pNA substrates at pH 9.0.

The pH-activity on the Suc-AAPF-pNA substrate, the pH-stability profile (residual activity after 2 hours at 37° C.), the temperature activity profile on Protazyme AK at pH 7.0 and the P1-specificity on 10 Suc-AAPF-pNA substrates at pH 9.0 for the S8 protease from Streptomyces sp. ACTE compared with the data for Savinase (protease from Bacillus lentus, Available from Novozymes A/S, Denmark) (SEQ ID NO 3) are also shown as FIGS. 1-4.

Other Characteristics for the Purified S8 Protease from Streptomyces sp. ACTE

The protease was inhibited by following known protease inhibitors: PMSF (Phenyl Methyl Sulphonyl Flouride), CI-2A (Chymotrypsin Inhibitor 2A from barley) and SSI (Streptomyces Subtilisin Inhibitor from Streptomyces albogriseolus).

The N-terminal sequence of the purified protein was determined by EDMAN degradation: ATQTNAP.

The molecular weight as determined by SDS-PAGE was approx. $M_r$=31 kDa.

The molecular weight determined by Mass spectroscopy analysis was 27702.4 Da.

The calculated weight of the mature protein corresponding to amino acids 1 to 279 of SEQ ID NO: 2 were 27702.1 Da, in excellent agreement with the experimentally determined mass.

Example 5. Automatic Mechanical Stress Assay (AMSA) for Laundry

In order to assess the wash performance in laundry washing experiments are performed, using the Automatic Mechanical Stress Assay (AMSA). The laundry experiments are conducted under the experimental conditions specified below:

| | |
|---|---|
| Detergent | Laundry liquid model detergent B |
| Detergent dosage | 2 g/l |
| Test solution volume | 140 μL detergent per slot; 20 μL enzyme per slot |
| pH | As is |
| Wash time | 20 minutes |
| Temperature | 40° C. and 20° C. |
| Water hardness | 16° dH $Ca^{2+}/Mg^{2+}$ 5:1 |

Test materials were as follows:

| | |
|---|---|
| Test material | EMPA117EH, Blood/milk/ink on Polyester/Cotton |
| | PC-03, Chocolate milk/soot on Polyester/Cotton |
| | CS-37, Full egg with pigment non-aged on Cotton |
| | C-10, Oil/milk/pigment on Cotton |

The protease prepared in Example 3 was tested in AMSA wash as described. The test was performed at both 20° C. and 40° C. and compared with a well-known protease for detergent, Savinase (SEQ ID NO 3), a protease derived from Bacillus lentus. The results are shown in table 6 to 7.

TABLE 6

| Swatch | Streptomyces sp. ACTE (20° C.) 5 nM | Savinase (20° C.) 5 nM | Streptomyces sp. ACTE (40° C.) 5 nM | Savinase (40° C.) 5 nM |
|---|---|---|---|---|
| PC-03 | 3 | 2 | 19 | 7 |
| C-10 | 4 | 1 | 9 | 0 |
| EMPA117EH | 1 | 0 | 32 | 4 |
| CS-37 | 6 | 10 | 5 | 7 |

TABLE 7

| Swatch | Streptomyces sp. ACTE (20° C.) 30 nM | Savinase (20° C.) 30 nM | Streptomyces sp. ACTE (40° C.) 30 nM | Savinase (40° C.) 30 nM |
|---|---|---|---|---|
| PC-03 | 13 | 6 | 40 | 20 |
| C-10 | 14 | 6 | 18 | 8 |
| EMPA117EH | 19 | 7 | 58 | 29 |
| CS-37 | 15 | 13 | 12 | 9 |

The results show that the Streptomyces sp. ACTE S8 protease showed good performance on all four stains at both 20° C. and 40° C.

Example 6. Automatic Mechanical Stress Assay (AMSA) for Laundry

The wash performance of S8 protease from Streptomyces sp. ACTE was tested using 2 different liquid detergents and a powder detergent at 2 different wash temperatures on 4 different technical stains using the Automatic Mechanical Stress Assay.

The experiments were conducted as described in the AMSA for laundry method using a single cycle wash procedure, with the detergent composition and swatches described in table 1 and the experimental conditions as specified in table 8 below. And the results are shown in table 9 and 10.

TABLE 8

| Experimental conditions for laundry experiments | |
|---|---|
| Detergent dosage | Laundry powder model detergent A 2.5 g/L, Laundry liquid model detergent B 2 g/L & 8 g/L or Unilever Persil Small&Mighty 1.33 g/L |
| Test solution volume | 160 micro L |
| pH | As is |
| Wash time | 20 minutes |
| Temperature | 20° C. or 40° C. |
| Water hardness | 15° dH |
| Protease concentration | 30 nm |
| Swatch | PC-05, PC-03, CS-37, C-10 |

Water hardness was adjusted to 15° dH by addition of $CaCl_2$, $MgCl_2$, and $NaHCO_3$ ($Ca^{2+}:Mg^{2+}:CO_3^-$=4:1:7.5) to the test system. After washing the textiles were flushed in tap water and dried.

TABLE 9

Delta intensity value of detergent containing S8 protease from Streptomyces sp. ACTE compared to detergent without protease at 20° C.

| Swatch | Detergent A (2.5 g/L) at 20° C. | Small&Mighty, Persil, Unilever (1.33 g/L) at 20° C. | Detergent B (2 g/L) at 20° C. | Detergent B (8 g/L) at 20° C. |
|---|---|---|---|---|
| PC-03 | 18 | 23 | 6 | 14 |
| C-10 | 12 | 9 | 8 | 11 |
| PC-05 | 50 | 18 | 18 | 40 |
| CS-37 | 6 | 11 | 7 | 7 |

The results show that detergent containing S8 protease from Streptomyces sp. ACTE is more effective at removing stains compared to detergent without protease. The S8 protease from Streptomyces sp. ACTE is effective at removing all four stains at 20° C., and especially effective at removing blood, milk and ink stains.

TABLE 10

Delta intensity value of detergent containing S8 protease from *Streptomyces* sp. ACTE ccompared to detergent without protease at 40° C.

| Swatch | Detergent A (2.5 g/L) at 40° C. | Small&Mighty, Persil, Unilever (1.33 g/L) at 40° C. | Detergent B (2 g/L) at 40° C. | Detergent B (8 g/L) at 40° C. |
|---|---|---|---|---|
| PC-03 | 41 | 10 | 5 | 35 |
| C-10 | 25 | 20 | 15 | 24 |
| PC-05 | 80 | 38 | 33 | 71 |
| CS-37 | 3 | 6 | 10 | 7 |

The results show that detergent containing S8 protease from *Streptomyces* sp. ACTE is more effective at removing stains compared to detergent without protease. The S8 protease from *Streptomyces* sp. ACTE is effective at removing all four stains at 40° C., and especially effective at removing blood, milk and ink stains Example 7. Mini Wash in Liquid Detergent Experimental Conditions

TABLE 11

| Detergents | Laundry liquid model detergent B |
|---|---|
| Dosage | 2 g/L and 8 g/L |
| Temperature | 20° C. |
| Enzymes | Savinase (Bacillus lentus protease) (SEQ ID NO 3) Protease from Example 3 |
| Enzyme dosage | 10-30-60-nM |
| Wash time | 20 min |
| Rinse time | 10 min |
| Stain/swatch | PC-05Blood/milk/ink on Polyester/Cotton |
| pH | As is |
| Test method | |

The experiment was run as a dual determination in the miniwash robot set-up on PC-05 swatch at 20° C. and 15° dH.

Water hardness was adjusted to 15° dH by addition of $CaCl_2$, $MgCl_2$, and $NaHCO_3$ ($Ca^{2+}:Mg^{2+}:CO_3^-=4:1:7.5$) to the test system. After washing the textiles were flushed in tap water and dried.

Test materials are obtained from Center for Testmaterials BV, P.O. Box 120, 3133 KT Vlaardingen, the Netherlands The textiles are subsequently air-dried and the wash performance is measured as the brightness of the color of these textiles. Brightness can also be expressed as the Remission (R), which is a measure for the light reflected or emitted from the test material when illuminated with white light. The Remission (R) of the textiles is measured at 460 nm using a Zeiss MCS 521 VIS spectrophotometer. The measurements are done according to the manufacturer's protocol.

The performance of the *Streptomyces* sp. ACTE is compared to the performance of Savinase (reference) (SEQ ID NO 3) at 10 nM, 30 nM and 60 nM protease concentration by calculating the relative performance:

$$RP=(R_{VARIANT}-R_{BLANK})/(R_{REFERENCE}-R_{BLANK})$$

An enzyme is considered to exhibit improved wash performance, if it performs better than the reference, which has a RP=1. Therefore an RP>1 shows an improved wash performance.

Results and Discussion:

The following table 12 shows the "Improvement factor/relative performance" of the enzyme of Example 3 with Savinase (SEQ ID NO 3) (Protease from *Bacillus lentus*, commercially available from Novozymes A/S, Denmark) as reference.

TABLE 12

| Detergent | Enzyme concentration | | |
|---|---|---|---|
| concentration | 10 nM | 30 nM | 60 nM |
| 2 g/l | 4.1 | 2.8 | 1.9 |

The results shows that the the *Streptomyces* sp. ACTE S8 protease performs better than Savinase in particular at low detergent concentration.

Example 8. AMSA Wash Performance of S8 Protease *Streptomyces* sp. ACTE in Different Water Hardness's and Protease Concentrations Using a Liquid Detergent The wash performance of S8 protease *Streptomyces* sp. ACTE was tested using a liquid detergent in 3 different water hardness's and 2 different enzyme concentrations on 3 different technical stains using the Automatic Mechanical Stress Assay.

The experiments were conducted as described in the AMSA for laundry method using a single cycle wash procedure, with the detergent composition and swatches described in Table 1 and the experimental conditions as specified in Table 13 below.

TABLE 13

Experimental conditions for AMSA for Tables 14 to 19.

| Test solution | 2 g/L Laundry liquid model detergent B |
|---|---|
| Test solution volume | 160 micro L |
| pH | As is |
| Wash time | 20 minutes |
| Temperature | 20 or 40° C. |
| Protease concentration | 0 (blank), 5 nM or 30 nM |
| Swatch | EMPA117EH, PC-03, C-10 |

Water hardness was adjusted to 6, 16 or 24° dH by addition of $CaCl_2$ and $MgCl_2$, ($Ca^{2+}:Mg^{2+}=5:1$) to the test system. After washing the textiles were flushed in tap water and dried.

TABLE 14

Delta intensity enzyme value of detergent containing S8 protease *Streptomyces* sp. ACTE or Savinase compared to detergent without protease on EMPA117EH swatches at 20° C.

| | Enzyme conc. | | | | | |
|---|---|---|---|---|---|---|
| Water hardness | 5 nM 6° dH | 5 nM 16° dH | 5 nM 24° dH | 30 nM 6° dH | 30 nM 16° dH | 30 nM 24° dH |
| Savinase | 0.91 | 3.00 | 2.24 | 8.72 | 9.89 | 12.28 |
| *Streptomyces* sp. ACTE | 5.01 | 5.42 | 4.45 | 20.51 | 22.81 | 18.84 |

The results show that detergent containing S8 protease *Streptomyces* sp. ACTE is especially effective at removing blood/milk/ink on cotton/polyester stains in low to medium water hardness's both compared to detergent without protease and to detergent containing Savinase.

TABLE 15

Delta intensity enzyme value of detergent containing
Streptomyces sp. ACTE or Savinase compared to detergent
without protease on PC-03 swatches at 20° C.

| | Enzyme conc. | | | | | |
|---|---|---|---|---|---|---|
| Water hardness | 5 nM 6° dH | 5 nM 16° dH | 5 nM 24° dH | 30 nM 6° dH | 30 nM 16° dH | 30 nM 24° dH |
| Savinase | 2.00 | 0.83 | 3.06 | 7.07 | 7.26 | 9.02 |
| Streptomyces sp. ACTE | 3.70 | 2.74 | 4.51 | 15.13 | 15.02 | 17.29 |

The results show that detergent containing S8 protease Streptomyces sp. ACTE is effective at removing chocolate-milk/ink on cotton/polyester stains in low to medium water hardness's both compared to detergent without protease and to detergent containing Savinase.

TABLE 16

Delta intensity enzyme value of detergent containing S8
protease Streptomyces sp. ACTE or Savinase compared
to detergent without protease on C-10 swatches at 20° C.

| | Enzyme conc. | | | | | |
|---|---|---|---|---|---|---|
| Water hardness | 5 nM 6° dH | 5 nM 16° dH | 5 nM 24° dH | 30 nM 6° dH | 30 nM 16° dH | 30 nM 24° dH |
| Savinase | 4.00 | 1.93 | 3.90 | 6.16 | 3.36 | 7.90 |
| Streptomyces sp. ACTE | 3.44 | 2.60 | 5.80 | 13.20 | 11.13 | 12.53 |

The results show that detergent containing S8 protease Streptomyces sp. ACTE is effective at removing oil/milk/pigment stains in low to medium water hardness's both compared to detergent without protease and to detergent containing Savinase.

TABLE 17

Delta intensity enzyme value of detergent containing S8 protease
Streptomyces sp. ACTE or Savinase compared to detergent
without protease on EMPA117EH swatches at 40° C.

| | Enzyme conc. | | | | | |
|---|---|---|---|---|---|---|
| Water hardness | 5 nM 6° dH | 5 nM 16° dH | 5 nM 24° dH | 30 nM 6° dH | 30 nM 16° dH | 30 nM 24° dH |
| Savinase | 2.63 | 6.21 | 16.76 | 22.19 | 21.18 | 49.54 |
| Streptomyces sp. ACTE | 22.25 | 21.85 | 32.56 | 57.31 | 52.03 | 59.50 |

The results show that detergent containing S8 protease Streptomyces sp. ACTE is especially effective at removing blood/milk/ink on cotton/polyester stains in low to medium water hardness's both compared to detergent without protease and to detergent containing Savinase.

TABLE 18

Delta intensity enzyme value of detergent containing
Streptomyces sp. ACTE or Savinase compared to detergent
without protease on PC-03 swatches at 40° C.

| | Enzyme conc. | | | | | |
|---|---|---|---|---|---|---|
| Water hardness | 5 nM 6° dH | 5 nM 16° dH | 5 nM 24° dH | 30 nM 6° dH | 30 nM 16° dH | 30 nM 24° dH |
| Savinase | 2.84 | 5.22 | 5.76 | 15.49 | 18.02 | 20.06 |
| Streptomyces sp. ACTE | 15.96 | 16.64 | 16.30 | 31.10 | 27.61 | 31.10 |

The results show that detergent containing S8 protease Streptomyces sp. ACTE is especially effective at removing chocolate-milk/ink on cotton/polyester stains in low to medium water hardness's at 40° C. both compared to detergent without protease and to detergent containing Savinase.

TABLE 19

Delta intensity enzyme value of detergent containing S8
protease Streptomyces sp. ACTE or Savinase compared
to detergent without protease on C-10 swatches at 40° C.

| | Enzyme conc. | | | | | |
|---|---|---|---|---|---|---|
| Water hardness | 5 nM 6° dH | 5 nM 16° dH | 5 nM 24° dH | 30 nM 6° dH | 30 nM 16° dH | 30 nM 24° dH |
| Savinase | 4.47 | 4.77 | 6.35 | 10.81 | 13.07 | 17.81 |
| Streptomyces sp. ACTE | 15.00 | 13.29 | 13.94 | 25.84 | 20.60 | 22.75 |

The results show that detergent containing S8 protease Streptomyces sp. ACTE is effective at removing oil/milk/pigment stains in low to medium water hardness's at 40° C. both compared to detergent without protease and to detergent containing Savinase.

The invention claimed is:

1. A detergent composition comprising one or more detergent components and an isolated polypeptide comprising a sequence with protease activity, wherein the sequence having protease activity has at least 95% sequence identity but less than 100% sequence identity to the mature polypeptide of SEQ ID NO: 2, wherein the sequence having protease activity has improved wash performance compared to the protease of SEQ ID NO: 3.

2. The detergent composition of claim 1, wherein the sequence has at least 97% sequence identity to the mature sequence of SEQ ID NO: 2.

3. The detergent composition of claim 1, wherein the sequence has at least 98% sequence identity to the mature sequence of SEQ ID NO: 2.

4. The detergent composition of claim 1, wherein the sequence has at least 99% sequence identity to the mature sequence of SEQ ID NO: 2.

5. The detergent composition of claim 1, wherein the sequence is the mature sequence of SEQ ID NO: 2.

6. The detergent composition of claim 1, wherein the sequence is a fragment that has protease activity.

7. The detergent composition of claim 1, further comprising one or more additional enzymes selected from the group consisting of amylase, arabinase, carbohydrase, cutinase, cellulase, galactanase, lipase, mannanase, oxidase, pectinase, peroxidase, protease, xylanase, and combinations thereof.

8. The detergent composition of claim 1, further comprising a protease inhibitor.

9. The detergent composition of claim 8, wherein the protease inhibitor is 4-formylphenyl boronic acid (4-FPBA) or a peptide aldehyde.

10. The detergent composition of claim 1, which is in the form of a homogenous tablet, a tablet having two or more layers, a pouch having one or more compartments, a regular or compact powder, a granule, or a regular, compact or concentrated liquid.

11. The detergent composition of claim 1, which is in a form of a powder.

12. The detergent composition of claim 1, which is in a form of a granulate.

13. The detergent composition of claim 1, which is in a form of a liquid.

14. The detergent composition of claim 1, which is formulated for automatic dishwash.

15. A method for degrading or removing proteinaceous materials from a textile or a hard surface comprising treating the textile or the hard surface with the detergent composition of claim 1.

16. A detergent composition comprising one or more detergent components and an isolated polypeptide comprising a sequence with protease activity, wherein the sequence having protease activity has at least 95% sequence identity but less than 100% sequence identity to the mature polypeptide of SEQ ID NO: 2, wherein the sequence having protease activity has improved wash performance compared to the protease of SEQ ID NO: 3, and wherein the composition is suitable for laundering of textiles or for cleaning hard surfaces.

* * * * *

SEQUENCE LISTING

```
<160> NUMBER OF SEQ ID NOS: 3

<210> SEQ ID NO 1
<211> LENGTH: 1185
<212> TYPE: DNA
<213> ORGANISM: Artificial
<220> FEATURE:
<223> OTHER INFORMATION: Synthetic gene
<220> FEATURE:
<221> NAME/KEY: CDS
<222> LOCATION: (1)..(1185)
<220> FEATURE:
<221> NAME/KEY: sig_peptide
```

<222> LOCATION: (1)..(81)
<220> FEATURE:
<221> NAME/KEY: mat_peptide
<222> LOCATION: (349)..(1185)

<400> SEQUENCE: 1

| | | | | | | | | | | | | | | | |
|---|---|---|---|---|---|---|---|---|---|---|---|---|---|---|---|
| atg | aag | aaa | ccg | ttg | ggg | aaa | att | gtc | gca | agc | acc | gca | cta | ctc | 45 |
| Met | Lys | Lys | Pro | Leu | Gly | Lys | Ile | Val | Ala | Ser | Thr | Ala | Leu | Leu | |
| | -115 | | | | -110 | | | | -105 | | | | | | |
| att | tct | gtt | gct | ttt | agt | tca | tcg | atc | gca | tcg | gct | gct | cag | cct | gaa | 93 |
| Ile | Ser | Val | Ala | Phe | Ser | Ser | Ser | Ile | Ala | Ser | Ala | Ala | Gln | Pro | Glu |
| | -100 | | | | | -95 | | | | -90 | | | | | |
| ggt | cgc | gtt | tta | cat | gca | cag | gct | gct | gaa | gct | gtt | cct | ggt | agc | tac | 141 |
| Gly | Arg | Val | Leu | His | Ala | Gln | Ala | Ala | Glu | Ala | Val | Pro | Gly | Ser | Tyr |
| -85 | | | | -80 | | | | -75 | | | | -70 | | | |
| att | gta | aca | ttg | aaa | cct | act | agc | ggt | ttc | aaa | gct | tct | gca | aca | gaa | 189 |
| Ile | Val | Thr | Leu | Lys | Pro | Thr | Ser | Gly | Phe | Lys | Ala | Ser | Ala | Thr | Glu |
| | | | -65 | | | | -60 | | | | -55 | | | | |
| gga | aaa | caa | ctt | att | gct | ggc | tac | gga | ggt | cgt | atc | act | cgt | act | tat | 237 |
| Gly | Lys | Gln | Leu | Ile | Ala | Gly | Tyr | Gly | Gly | Arg | Ile | Thr | Arg | Thr | Tyr |
| | | -50 | | | | -45 | | | | -40 | | | | | |
| act | tca | gct | ctt | aac | gga | tac | gct | gct | gct | tta | agc | tct | gca | gaa | gca | 285 |
| Thr | Ser | Ala | Leu | Asn | Gly | Tyr | Ala | Ala | Ala | Leu | Ser | Ser | Ala | Glu | Ala |
| | -35 | | | | -30 | | | | -25 | | | | | | |
| cgc | cgt | ttg | gct | gca | gat | cca | gca | gtt | gaa | tct | gta | gag | cag | gat | caa | 333 |
| Arg | Arg | Leu | Ala | Ala | Asp | Pro | Ala | Val | Glu | Ser | Val | Glu | Gln | Asp | Gln |
| -20 | | | | -15 | | | | -10 | | | | | | | |
| aaa | gtt | cat | gct | acg | gca | act | caa | aca | aat | gcg | cca | tgg | ggc | ttg | gac | 381 |
| Lys | Val | His | Ala | Thr | Ala | Thr | Gln | Thr | Asn | Ala | Pro | Trp | Gly | Leu | Asp |
| -5 | | | -1 | 1 | | | | 5 | | | | | 10 | | |
| cgc | att | gac | caa | gca | aat | ctt | ccg | ctt | aac | ggc | act | tac | act | tat | cca | 429 |
| Arg | Ile | Asp | Gln | Ala | Asn | Leu | Pro | Leu | Asn | Gly | Thr | Tyr | Thr | Tyr | Pro |
| | | 15 | | | | 20 | | | | 25 | | | | | |
| gat | tct | gct | gga | ggt | ggt | act | aca | gtt | tac | gtt | ctt | gac | act | ggc | gta | 477 |
| Asp | Ser | Ala | Gly | Gly | Gly | Thr | Thr | Val | Tyr | Val | Leu | Asp | Thr | Gly | Val |
| | 30 | | | | 35 | | | | 40 | | | | | | |
| cgc | atc | aca | cac | caa | caa | atc | tct | ggt | cgc | gca | tct | tac | ggt | tac | gat | 525 |
| Arg | Ile | Thr | His | Gln | Gln | Ile | Ser | Gly | Arg | Ala | Ser | Tyr | Gly | Tyr | Asp |
| 45 | | | | 50 | | | | 55 | | | | | | | |
| ttc | gtt | gac | aac | gac | gct | gta | gct | caa | gac | ggt | gct | ggc | cat | gga | act | 573 |
| Phe | Val | Asp | Asn | Asp | Ala | Val | Ala | Gln | Asp | Gly | Ala | Gly | His | Gly | Thr |
| 60 | | | | 65 | | | | 70 | | | | 75 | | | |
| cat | gtt | gct | aca | aca | gtt | gct | gga | tct | aca | tac | ggt | gta | gcg | aag | aaa | 621 |
| His | Val | Ala | Thr | Thr | Val | Ala | Gly | Ser | Thr | Tyr | Gly | Val | Ala | Lys | Lys |
| | | | 80 | | | | 85 | | | | 90 | | | | |
| gcg | aaa | atc | gta | gct | gta | cgt | gtt | tta | gac | aac | aac | ggt | tct | gga | act | 669 |
| Ala | Lys | Ile | Val | Ala | Val | Arg | Val | Leu | Asp | Asn | Asn | Gly | Ser | Gly | Thr |
| | | 95 | | | | 100 | | | | 105 | | | | | |
| act | gca | ggt | gtt | att | gca | ggc | gta | gat | tgg | att | aca | gca | aac | cat | gtt | 717 |
| Thr | Ala | Gly | Val | Ile | Ala | Gly | Val | Asp | Trp | Ile | Thr | Ala | Asn | His | Val |
| | 110 | | | | 115 | | | | 120 | | | | | | |
| gct | agc | tct | gtt | gca | aac | gta | tca | ctt | ggt | gga | ggt | cct | tct | act | gca | 765 |
| Ala | Ser | Ser | Val | Ala | Asn | Val | Ser | Leu | Gly | Gly | Gly | Pro | Ser | Thr | Ala |
| | 125 | | | | 130 | | | | 135 | | | | | | |
| tta | gat | gat | gcg | gtt | cgt | cgc | tca | att | gct | tca | ggt | gtt | act | tac | tct | 813 |
| Leu | Asp | Asp | Ala | Val | Arg | Arg | Ser | Ile | Ala | Ser | Gly | Val | Thr | Tyr | Ser |
| 140 | | | | 145 | | | | 150 | | | | 155 | | | |
| att | gcg | gca | gga | aac | agc | ggt | gct | cca | gca | tct | ggt | tat | tct | cct | gca | 861 |
| Ile | Ala | Ala | Gly | Asn | Ser | Gly | Ala | Pro | Ala | Ser | Gly | Tyr | Ser | Pro | Ala |
| | | 160 | | | | 165 | | | | 170 | | | | | |

```
cgt gtt gac act gct atc act gtt ggc gca acg aca cgt act gac gca     909
Arg Val Asp Thr Ala Ile Thr Val Gly Ala Thr Thr Arg Thr Asp Ala
            175                 180                 185 cgt gcc tct tac tct aac tac ggt cct gtt gta gac atc ttt gct cca     957
Arg Ala Ser Tyr Ser Asn Tyr Gly Pro Val Val Asp Ile Phe Ala Pro
            190                 195                 200 gga tca gac atc act gct gga tgg aac act tct gac aca gca act tac    1005
Gly Ser Asp Ile Thr Ala Gly Trp Asn Thr Ser Asp Thr Ala Thr Tyr
            205                 210                 215 aca gga tca ggt acg tca ttc gct gct cca cat gtt gca gga gct gct    1053
Thr Gly Ser Gly Thr Ser Phe Ala Ala Pro His Val Ala Gly Ala Ala
220             225                 230                 235 gca gtt tac ttg aca aac cat cca gga tca cca gct gcg gtt gct        1101
Ala Val Tyr Leu Thr Asn His Pro Gly Ser Pro Ala Ala Val Ala
                240                 245                 250 tca gca ttg gta aat ggc gct act tca aac gtt ctt act ggc atc ggc    1149
Ser Ala Leu Val Asn Gly Ala Thr Ser Asn Val Leu Thr Gly Ile Gly
            255                 260                 265 act ggt tct cct aac aaa ttg ctt aag ctt gtt cct                    1185
Thr Gly Ser Pro Asn Lys Leu Leu Lys Leu Val Pro
            270                 275

<210> SEQ ID NO 2
<211> LENGTH: 395
<212> TYPE: PRT
<213> ORGANISM: Artificial
<220> FEATURE:
<223> OTHER INFORMATION: Synthetic Construct

<400> SEQUENCE: 2

Met Lys Lys Pro Leu Gly Lys Ile Val Ala Ser Thr Ala Leu Leu
    -115            -110                -105

Ile Ser Val Ala Phe Ser Ser Ser Ile Ala Ser Ala Ala Gln Pro Glu
        -100            -95                 -90

Gly Arg Val Leu His Ala Gln Ala Ala Glu Ala Val Pro Gly Ser Tyr
-85             -80                 -75                 -70

Ile Val Thr Leu Lys Pro Thr Ser Gly Phe Lys Ala Ser Ala Thr Glu
                -65                 -60                 -55

Gly Lys Gln Leu Ile Ala Gly Tyr Gly Gly Arg Ile Thr Arg Thr Tyr
                -50                 -45                 -40

Thr Ser Ala Leu Asn Gly Tyr Ala Ala Ala Leu Ser Ser Ala Glu Ala
            -35                 -30                 -25

Arg Arg Leu Ala Ala Asp Pro Ala Val Glu Ser Val Glu Gln Asp Gln
    -20                 -15                 -10

Lys Val His Ala Thr Ala Thr Gln Thr Asn Ala Pro Trp Gly Leu Asp
-5                  -1  1               5                   10

Arg Ile Asp Gln Ala Asn Leu Pro Leu Asn Gly Thr Tyr Thr Tyr Pro
                15                  20                  25

Asp Ser Ala Gly Gly Gly Thr Thr Val Tyr Val Leu Asp Thr Gly Val
            30                  35                  40

Arg Ile Thr His Gln Gln Ile Ser Gly Arg Ala Ser Tyr Gly Tyr Asp
        45                  50                  55

Phe Val Asp Asn Asp Ala Val Ala Gln Asp Gly Ala Gly His Gly Thr
60                  65                  70                  75

His Val Ala Thr Thr Val Ala Gly Ser Thr Tyr Gly Val Ala Lys Lys
                80                  85                  90

Ala Lys Ile Val Ala Val Arg Val Leu Asp Asn Asn Gly Ser Gly Thr
            95                  100                 105
```

-continued

```
Thr Ala Gly Val Ile Ala Gly Val Asp Trp Ile Thr Ala Asn His Val
        110                 115                 120

Ala Ser Ser Val Ala Asn Val Ser Leu Gly Gly Gly Pro Ser Thr Ala
    125                 130                 135

Leu Asp Asp Ala Val Arg Arg Ser Ile Ala Ser Gly Val Thr Tyr Ser
140                 145                 150                 155

Ile Ala Ala Gly Asn Ser Gly Ala Pro Ala Ser Gly Tyr Ser Pro Ala
                160                 165                 170

Arg Val Asp Thr Ala Ile Thr Val Gly Ala Thr Thr Arg Thr Asp Ala
            175                 180                 185

Arg Ala Ser Tyr Ser Asn Tyr Gly Pro Val Val Asp Ile Phe Ala Pro
        190                 195                 200

Gly Ser Asp Ile Thr Ala Gly Trp Asn Thr Ser Asp Thr Ala Thr Tyr
    205                 210                 215

Thr Gly Ser Gly Thr Ser Phe Ala Ala Pro His Val Ala Gly Ala Ala
220                 225                 230                 235

Ala Val Tyr Leu Thr Asn His Pro Gly Ser Ser Pro Ala Ala Val Ala
                240                 245                 250

Ser Ala Leu Val Asn Gly Ala Thr Ser Asn Val Leu Thr Gly Ile Gly
            255                 260                 265

Thr Gly Ser Pro Asn Lys Leu Leu Lys Leu Val Pro
        270                 275

<210> SEQ ID NO 3
<211> LENGTH: 269
<212> TYPE: PRT
<213> ORGANISM: Bacillus lentus

<400> SEQUENCE: 3

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
```

-continued

```
            195                 200                 205
Ala Ser Leu Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```